(12) United States Patent
Finger et al.

(10) Patent No.: US 11,865,360 B2
(45) Date of Patent: Jan. 9, 2024

(54) METHODS AND SYSTEMS FOR SHAPING THE RADIATION DISTRIBUTION PROFILE OF A PROTECTED RADIATION SOURCE USED FOR TREATING MEDICAL CONDITIONS

(71) Applicant: IP LIBERTY VISION CORPORATION, Suite, NY (US)

(72) Inventors: Paul T. Finger, New York, NY (US); Toby Welles, New York, NY (US)

(73) Assignee: IP LIBERTY VISION CORPORATION, New York, NY (US)

(*) Notice: Subject to any disclaimer, the term of this patent is extended or adjusted under 35 U.S.C. 154(b) by 100 days.

(21) Appl. No.: 17/505,601

(22) Filed: Oct. 19, 2021

(65) Prior Publication Data

US 2022/0266059 A1   Aug. 25, 2022

Related U.S. Application Data

(63) Continuation of application No. 16/983,675, filed on Aug. 3, 2020, now abandoned, which is a continuation of application No. 16/210,623, filed on Dec. 5, 2018, now abandoned.

(60) Provisional application No. 62/594,997, filed on Dec. 5, 2017.

(51) Int. Cl.
*A61N 5/10* (2006.01)

(52) U.S. Cl.
CPC ......... *A61N 5/1014* (2013.01); *A61N 5/1007* (2013.01); *A61N 5/1031* (2013.01); *A61N 2005/1005* (2013.01); *A61N 2005/1019* (2013.01)

(58) Field of Classification Search
CPC .......... A61N 2005/1025; A61N 5/1027; A61N 5/1017; A61N 5/1007; A61N 5/10; A61N 5/1001; A61N 2005/1094; A61N 2005/1024; A61N 2005/1005; A61N 2005/1019; A61N 5/1028; A61N 5/1014; G21G 4/04; G21G 4/06
See application file for complete search history.

(56) References Cited

U.S. PATENT DOCUMENTS

| | | | | |
|---|---|---|---|---|
| 2,517,568 A | * | 8/1950 | Hissong | A61F 9/007 600/7 |
| 2009/0156881 A1 | * | 6/2009 | Stokes | A61N 5/1017 600/7 |
| 2013/0317276 A1 | * | 11/2013 | D'Andrea | A61N 5/1067 600/2 |

* cited by examiner

*Primary Examiner* — Samuel G Gilbert
(74) *Attorney, Agent, or Firm* — Smith Tempel; Steven P. Wigmore

(57) ABSTRACT

A method and system may include a therapeutic agent having a radioactive source enclosed by a container. The container may be placed within a cavity of a medical device for treating animal tissue. The method and system allows a radioactive source to be manufactured in such a manner so as to control and spatially modulate the delivery of radiation doses to a treatment area of animal tissue, such as for tissue of humans. From the container, radiation doses and/or a radiation field are produced by the radiation source. The geometry and size of the radiation doses are controlled by the geometry of the container and the geometry of the radiation source as well as the type, number, and geometry of holes/slots in either the source material and/or a surface of the container.

20 Claims, 21 Drawing Sheets

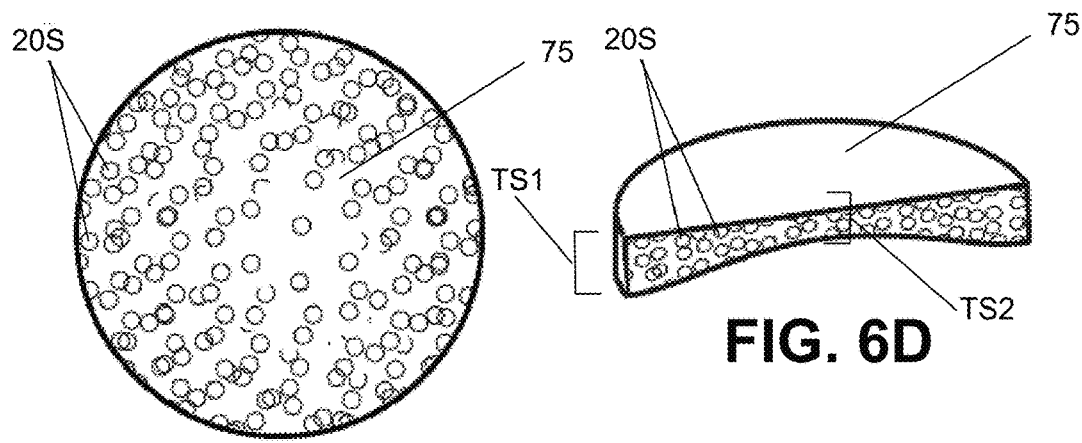
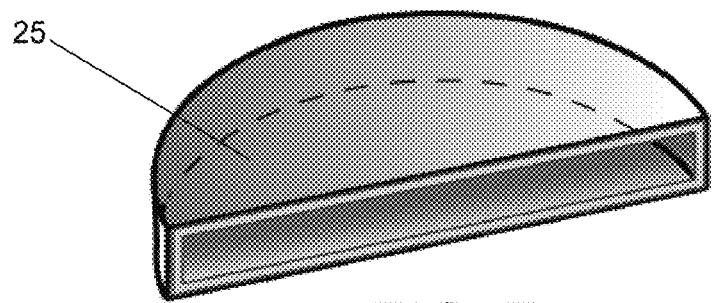
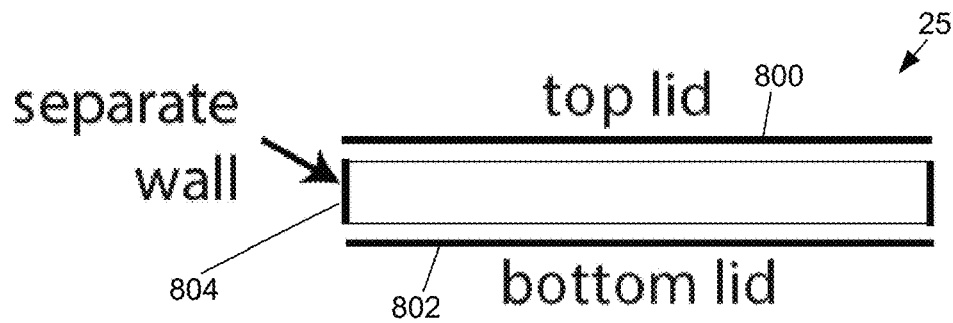
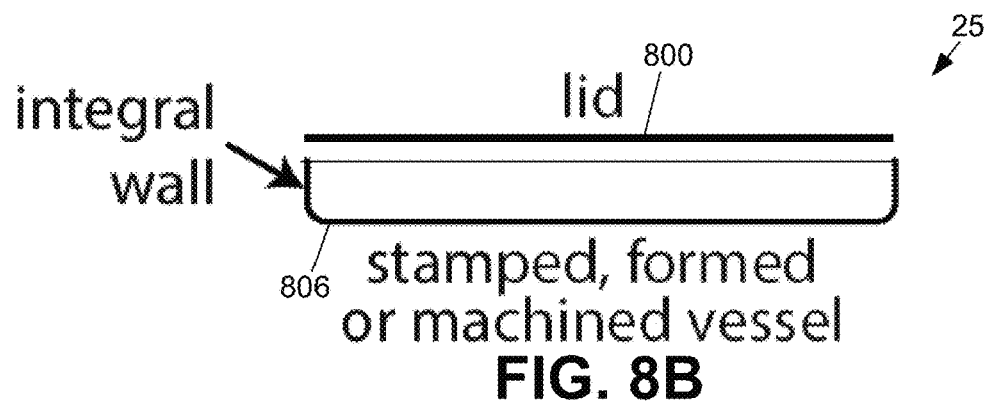

METHODS AND SYSTEMS FOR SHAPING THE RADIATION DISTRIBUTION PROFILE OF A PROTECTED RADIATION SOURCE USED FOR TREATING MEDICAL CONDITIONS

BACKGROUND OF THE INVENTION

It is well established that radiation can be used to treat a variety of medical conditions, and one of the chief means of delivering radiation for therapeutic uses is to place a source of radiation emissions adjacent to the area being treated. Depending on the attributes of the radiation source, the type of radiation, its intensity and its penetrating ability, all can be tailored to meet the specific therapeutic requirements of a given treatment area and condition. Such radiation can be beta, gamma or photon radiation including bremsstrahlung radiation.

Until now, treatments have used unsophisticated therapeutic agents referred to generally as radiation sources or sources. Such conventional radiation sources may have radiation dose distribution profiles that are not tailored to the unique needs of the specific volumetric configuration of a treatment area, such as for a posterior portion of an eye globe in the human body. Further, conventional radiation sources have typically been mass produced in ways that do not lend themselves to accommodating the variability present from one patient or condition to another.

Accordingly, there is a need in the art for radioactive sources that can be manufactured in such a manner so as to control and spatially modulate the delivery of radiation doses to the treatment area or volume. There is also a need in the art to produce radioactive sources which may have a geometry that is unique and/or tailored to the geometry of the treatment area or volume, such as forming a radioactive source which has a geometry similar to a geometry of a tumor formed on an organ of the human body.

SUMMARY OF THE DISCLOSURE

The method and system described herein may include a therapeutic agent comprising a radioactive source enclosed by a container. The container may be placed within a cavity of a medical device for treating animal tissue. The inventive method and system allows a radioactive source to be manufactured in such a manner so as to control and spatially modulate the delivery of radiation doses to a treatment area of animal tissue, such as for tissue of humans.

From the container, radiation doses and/or a radiation field is produced by the radiation source. The geometric profile and size of the radiation doses are controlled by the geometry of the container and the geometry of the radiation source as well as the type, number, and geometry of holes/slots in a top wall of the container.

Exemplary materials for the source may include, but are not limited to, $^{9}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi, just to name a few. The source may include any combination of these materials.

Controlling the distribution of the mass of the radionuclide source affords the ability to vary the specific output across the face of a source. This can have several results, the first being able to achieve greater uniformity of the isodose despite source geometries that would normally result in non-uniform activity levels based solely on the perimeter profile of the source. Another result could be the deliberate variation of the isodose across the face of the source to reflect the variable therapeutic dose requirements of a particular condition, patient or both.

Another way of controlling dose profiles is using manufacturing methods that would allow the selective deposition of variable amounts of a radionuclide-containing compound (including but not limited to such compounding agents as a polymer, adhesive, paint or ceramic) onto a uniform or shaped substrate material to form source. Current methods of so-called additive manufacturing techniques could be adapted to use radioactive compounds as the deposited medium.

The sources may be encapsulated in a secondary material, such as a container, to give greater protection from damage to the source; to prevent unwanted leaching or leakage of source material; or to provide shield of the animal tissue from non-biocompatible materials or unwanted radiation output. This encapsulation/container may be formed to control radiation effects by the following approaches: varying encapsulation/container thickness to partially, and/or selectively shield the source to control emissions through variable attenuation; vary the materials making up the encapsulation/container to selectively deliver differing emissions around the source; vary the contours of the encapsulation/container to control the internal position of the source within the capsule/container and thus the proximity of the source and dose rate delivered to the tissue treatment volume; shaping the encapsulation/container to control, focus or distribute radiation in a desired direction and/or intensity for therapeutic purposes.

The method and system may control radiation emitted by the source by forming the source with a disc-like geometry. The source may have a variable thickness. According to one exemplary embodiment, the source may have a disc-like geometry where a thickness in the geometrical central portion is thinner relative to the edge portion of the disc-like portion. Such a disc-like source geometry if having uniform mass across its area would produce a centrally biased dose distribution profile, whereas by reducing the amount of radionuclide mass in the central region, a more uniform dose output results. Further, in a general case, by varying the distribution of mass in selectively non-uniform patterns across the area of the source, one can create a dose output profile that is tailored to the specific, desired dosage pattern in a treatment situation that requires greater dose delivery in one portion of the treatment volume versus that in others.

The method and system may control radiation emitted by the source by forming the source with a disc-like geometry, where this disc-like geometry further has apertures or holes penetrating through the source. According to one exemplary embodiment, the apertures or holes may comprise a circular geometry. Further, according to one exemplary embodiment, the diameter of the apertures may be consistent. According to another exemplary embodiment, the apertures may have a range of different diameters. According to another exemplary embodiment, these apertures may comprise slots having a length and width dimension.

[FIG. 3-4D]

The method and system may also comprise a disc-like geometry having a sinusoidal cross-section. The method and system may also comprise a source having a variable thickness across its disc-like geometry that is encapsulated by a simple container having a uniform thickness and cylindrical geometry. The method and system may further comprise a source having a variable thickness across its disc-like geometry that is encapsulated by a simple container having cylindrical geometry which has a contoured face to match the disc-like geometry of the source.

The method and system may also comprise a radionuclide source where layers of radionuclide source material having have different perimeter profiles relative to each other and are stacked on top of each other. This stack arrangement of radionuclide source layers may be encapsulated by a simple container having a regular cylindrical geometry.

The method and system may comprise a composite source, with or without a substrate material. Both the source and substrate may be created by various methods of formation. The method and system may have a shaped substrate with molded or poured source material. The shaped source material may have a regular geometry or an irregular geometry. An irregular geometry means that the source may not have any lines of geometrical symmetry or far fewer geometrical lines of symmetry compared to the geometrical lines of symmetry for the container. Usually, a source with an irregular geometry will have an irregular geometry presented in its cross-sectional view. The container may have a regular, cylindrical shape for enclosing the radioactive source and thus, a symmetrical cross-sectional geometry.

The method and system may comprise beads, seeds, and/or microspheres that form a radioactive source to provide a unique, desired dose profile. The beads, seeds, and/or microspheres may have substantially similar geometries and sizes and/or different geometries and different sizes.

The method and system may comprise uniquely shaped containers which are formed by at least two walls. Each wall may comprise unique shielding characteristics in order to help shape radiation emitted by any radioactive source housed within the container.

The method and system may comprise a radioactive source having a geometry shaped to match a geometry of a tumor in an organ and a container shaped to match an outer wall of an organ, where the wall of the organ is not distorted by the tumor. The method and system may comprise a radioactive source having a geometry shaped to match a geometry of a tumor in the organ and a container shaped to match an outer wall of an organ, where the wall of the organ may be distorted by the tumor. The method and system may comprise a radioactive source having a first geometry and a container having a second geometry, where both the first and second geometry are shaped to match a geometry of a tumor growing external to the organ.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS in the Figures, like reference numerals refer to like parts throughout the various views unless otherwise indicated. For reference numerals with letter character designations such as "102A" or "102B", the letter character designations may differentiate two like parts or elements present in the same Figure. Letter character designations for reference numerals may be omitted when it is intended that a reference numeral to encompass all parts having the same reference numeral in all Figures.

FIG. 6C shows radioactive microspheres in a polymer matrix with activity/dose controlled by a molded thickness as illustrated in FIG. 6D;

FIG. 6D illustrates a polymer matrix having an edge thicknesses and a central thickness which may be similar to those of FIG. 1C;

FIG. 7 shows a capsule used for encapsulating radionuclide source materials;

FIG. 8A shows a three-piece assembly capsule which includes a lid, perimeter wall and substantially flat bottom;

FIG. 8B illustrates a two-piece capsule that comprises a lid which is attached to a bottom with an integral wall that is either a stamped formed element or a machined element;

DETAILED DESCRIPTION OF EXEMPLARY EMBODIMENTS

Figure 1A:
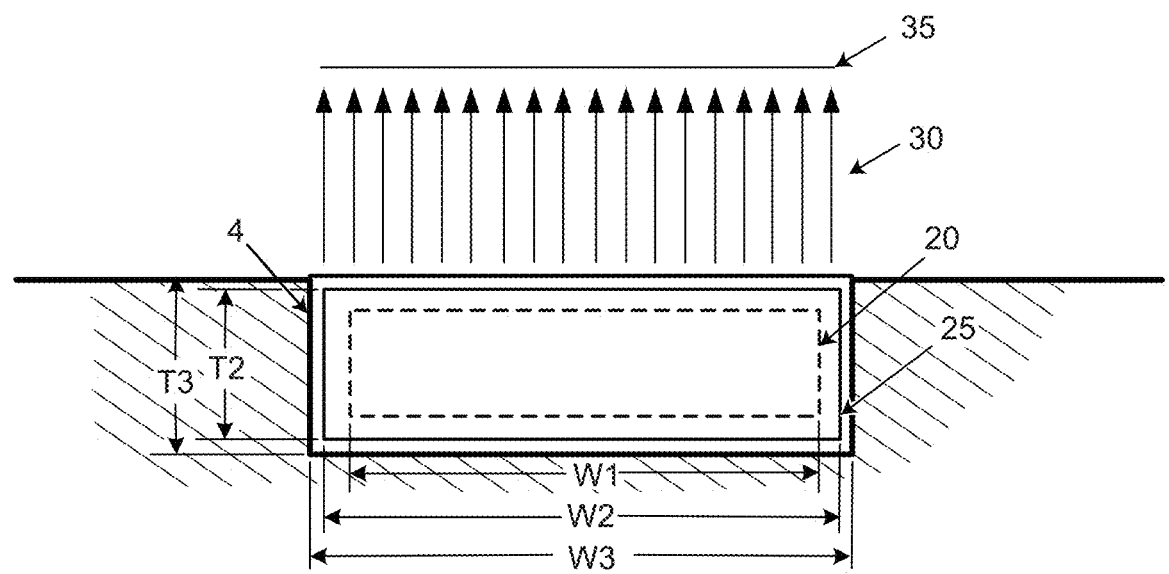
FIG. 1A illustrates a cross-sectional view of a radioactive source enclosed by a container according to one exemplary embodiment.
Figure 1B:
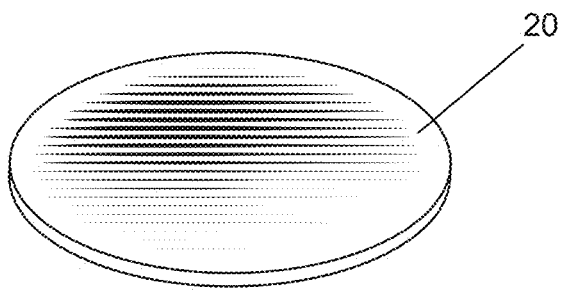
FIG. 1B shows a cylindrically shaped radionuclide source with a variable concentric thickness with denoted by dimensions which affects the dose profile of FIG. 1A.
Figure 1C:
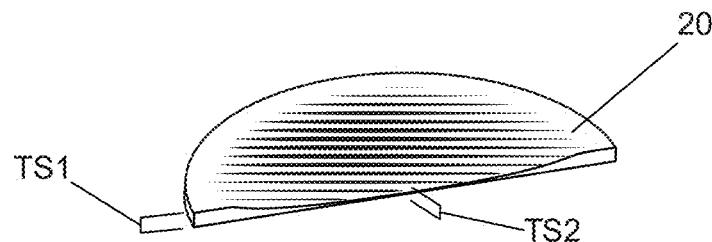
FIG. 1C illustrates a cross-sectional view of the same source shown in FIG. 1B where the edges of the source disc are thicker relative to the center which is thinner and has a dimension resulting in a concave shape on the large, facial surface of the source disc.
Figure 1D:
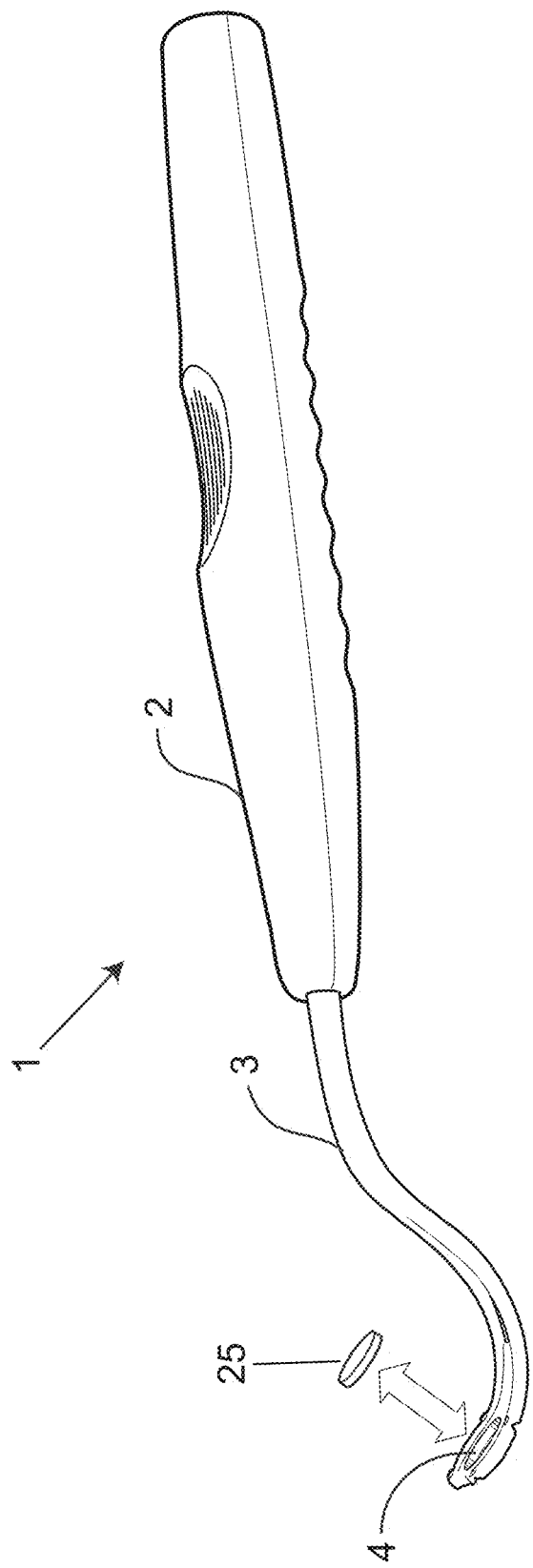
FIG. 1D illustrates an inventive method and system in the form of a therapeutic agent having a cylindrical container that is placed in a cavity of a wand for an ophthalmic treatment device.

Referring now to FIG. 1D, the inventive method and/or system may form a therapeutic agent referenced in commonly assigned U.S. patent application Ser. No. 14/243,623 filed on Apr. 2, 2014, where the entire contents of which are hereby incorporated by reference. The inventive therapeutic agent may have a cylindrical container 25 of FIG. 1A and it may be placed in a cavity 4 of a wand 3 having a handle 2 of FIG. 1D of an ophthalmic treatment device 1. However, the inventive therapeutic agent is not limited to ophthalmic treatment devices 1 and may be used in other medical devices as understood by one of ordinary skill in the art and as described in further detail below.

The inventive therapeutic agent may be included in other treatment devices for treating other organs in the human body besides the human eye, eye lids or orbit. Other organs besides the human eye may include, but are not limited to the following organs and organ systems: organs of digestion including, but not limited to, the stomach, liver, small intestine, large intestine, rectum, and anus; organs of respiration, including, but not limited to, the lungs, nose, trachea, and bronchi; organs of excretion, including, but not limited to, the kidneys, urinary bladder, and urethra; organs of circulation, including, but not limited to, the heart, blood vessels, and spleen; organs of the nervous system, including, but not limited to, the brain and spinal cord; organs of reproduction, including, but not limited to, the testis and penis in male, the uterus, ovaries & mammary glands in the female; organs of the endocrine system, including, but not limited to, the pituitary gland, adrenal, thyroid, pancreas, parathyroid, and prostate glands; organs of senses, including, but not limited to, the skin, tongue, nose, and ears; organs of the immune system, including, but not limited to, the spleen, thymus, and bone marrow; organs of metabolism, including, but not limited to, the liver, just to name a few.

Referring back to FIG. 1A, this figure illustrates a cross-sectional view of a therapeutic agent comprising a radioactive source 20 enclosed by a cylindrical container 25. The exemplary container 25 and radioactive source 20 illustrated in FIG. 1A each are shown with a cylindrical shape. However, other geometries for the source 20 and container 25 are possible and are within the scope of this disclosure as understood by one of ordinary skill in the art. The container 25 may be placed within a cavity 4 as illustrated in FIG. 1D. The inventive method and system has thus been devised to allow the radioactive source 20 to be manufactured in such a manner as to control and spatially modulate the delivery of radiation doses 30 to the treatment area.

From the container 25, radiation doses 30 and/or a radiation field 35 is produced by the radiation source 20. The geometry and size of the radiation doses 30 are controlled by the geometry of the container 25 and the geometry of the radiation source 20 as well as the type, number, and geometry of holes/slots [not shown in this FIG. 1A] in a top wall of the container 25.

As understood by one of ordinary skill in the art, the radiation field 35 illustrated in FIG. 1A is an over-simplification. Radiation, almost by definition is not linear. There usually exists at least Compton Scatter and photo-electric effects associated with radiation from a source and the source's resultant radiation field. The illustration of the radiation field 35 in FIG. 1 does not show penumbra, backscatter, and/or absorption which are generally present in all radiation fields.

A generally/substantially linear radiation distribution profile 35 is illustrated in FIG. 1A and is, but at least one, object/goal of the combination of the container 25 and source 20 compared to conventional radiation distribution profiles of conventional sources [not shown] which do not have substantially linear profiles and/or are un-even.

Exemplary materials for the source 20 may include, but are not limited to, $^{9}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi, just to name a few. The source 20 may include any combination of these materials as understood by one of ordinary skill in the art.

The source 20 may have a width dimension W1 between about 1.9 mm and about 21.9 mm. Meanwhile, the container 25 may have a width dimension W2 between about 2.0 mm and about 22.0 mm if the side wall of the container 25 is about 0.1 mil wide.

The cavity 4 may have a width dimension W3 which may be generally equal to the width dimension W2 of the container 25 plus a few mils, and thus, the width dimension W3 should range from between about 2.1 mm to about 22.1 mm, depending upon the size of the container 25. However, as understood by one of ordinary skill in the art, each of the structures 20, 25 may be tightly fitted within cavity 4, and thus, the width dimensions can closely approach each corresponding structure which may contain another structure.

The container 25 may also have a thickness dimension T2 between about 0.25 mm and about 1.00 mm. The cavity 4 may also have a thickness dimension T3 between about 0.75 mm and about 3.00 mm. The thickness of the source 20 will be described in further detail below in connection with FIG. 1C.

A variety of ways/methods/systems to control and spatially modulate the delivery of radiation doses 30 to a treatment area are outlined below. Briefly, modifications to the source 20 itself may be employed, its construction or production, along with modifications to its encapsulation/container 25 to both control and vary the spatial intensity and characteristics of delivered radiation dosages 30. For clarity, these approaches are presented below in three subsections with the attached Figures:

(1) Methods/Systems for Manufacturing and Processing of Radionuclide Materials for Source 20 to Shape Sources 20 in Ways that Will Control their Output.

These approaches to controlling the distribution of the mass of the radionuclide source 20 afford the ability to vary the specific output across the face of a source 20. This can have several results, the first being able to achieve greater uniformity of the isodose 35 despite source geometries that would normally result in non-uniform activity levels based solely on the perimeter profile of the source 20. Another result could be the deliberate variation of the isodose 35 across the face of the source 20 to reflect the variable therapeutic dose requirements of a particular condition, patient or both.

(2) Methods/Systems for Shaping Radionuclide Materials for Sources 20 in an Additive or Molded Manufacturing Process.

Another way of controlling dose profiles for the purposes mentioned above would be to use manufacturing methods that would allow the selective deposition of variable amounts of a radionuclide-containing compound (including but not limited to such compounding agents as a polymer, adhesive, paint or ceramic) onto a uniform or shaped substrate material to form source 20. Current methods of so-called additive manufacturing techniques could be adapted to use radioactive compounds as the deposited medium.

(3) Methods of Creating and Configuring Spatially Variable Dose-Rate Brachytherapy Sources 20.

Sources 20 are often encapsulated in a secondary material, such as a container 25, to give greater protection from damage to the source 20, prevention of unwanted leaching or leakage of source material, or to provide shield of the body from nonbiocompatible materials. The invention, according to several different exemplary embodiments described below, may use this encapsulation/container 25 to control radiation effects by the following approaches:

a. Variation of encapsulation/container 25 thickness to partially, and/or selectively shield the source to control emissions through variable attenuation.

b. Vary the materials making up the encapsulation/container 25 to selectively deliver differing emissions around the source 20.

c. Vary the contours of the encapsulation/container 25 to control the internal position of the source 20 within the capsule/container 25 and thus the proximity of the source 20 and dose rate delivered to the tissue treatment volume.

d. Shaping the encapsulation/container 25 to control, focus or distribute radiation 35 in a desired direction and/or intensity for therapeutic purposes.

(1) Ways to Process Radionuclide Source Material 20 to Control the Activity Profile Across the Source 20

FIG. 1B shows a cylindrically shaped radionuclide source 20 with a variable concentric thickness/width denoted by dimensions TS1 and TS2 (in FIG. 1C) which affects the dose profile 35 of FIG. 1A. As illustrated in FIG. 1C, which is a cross-sectional view of source 20, the edges having dimensions TS1 of the source disc 20 are thicker relative to the center which is thinner and has the dimension TS2 resulting in a concave shape on the large, facial surface of the source disc 20. Exemplary edge dimensions TS1 may be between about 0.25 mm and about 2.00 mm. Exemplary center dimensions TS2 may be between about 0.05 mm and about 1.00 mm. However, other ranges are possible and are included with thin the scope of this disclosure. Such an exemplary geometry would result in a largely uniform dose distribution 35 across the source 20 compared to a conventional source 20 [not shown] which may have a uniform thickness across its cross-section.

Figure 1E:
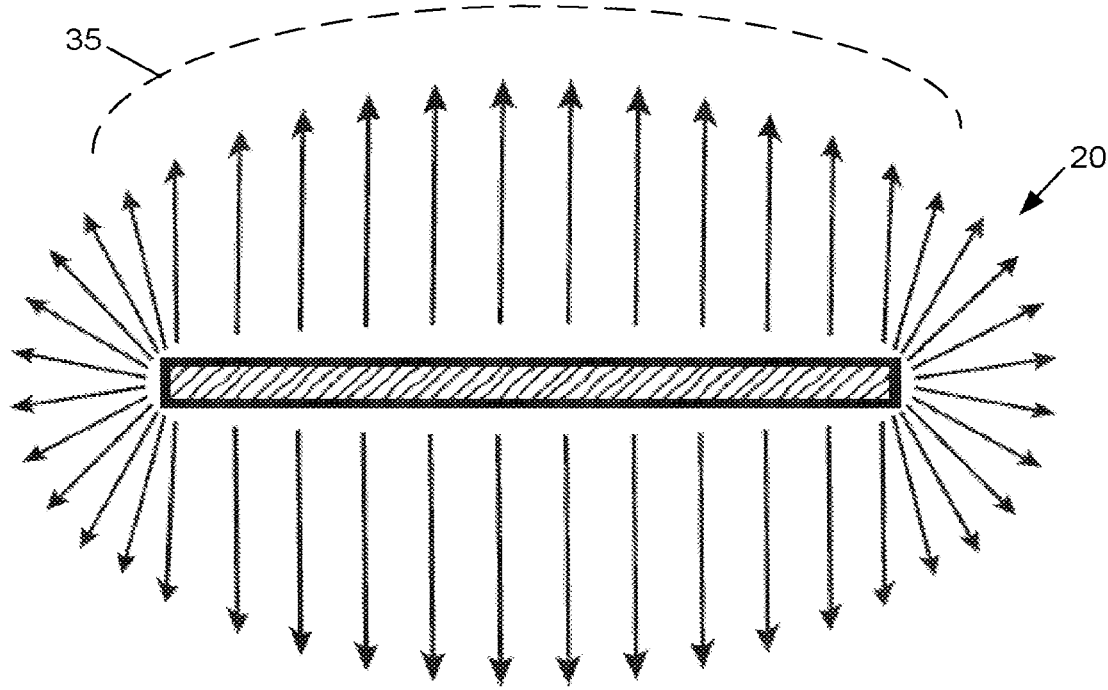
FIG. 1E illustrates a disc-like geometry for a radioactive source having a uniform mass across its area that may produce a centrally biased radiation/dose distribution profile.
Figure 1F:
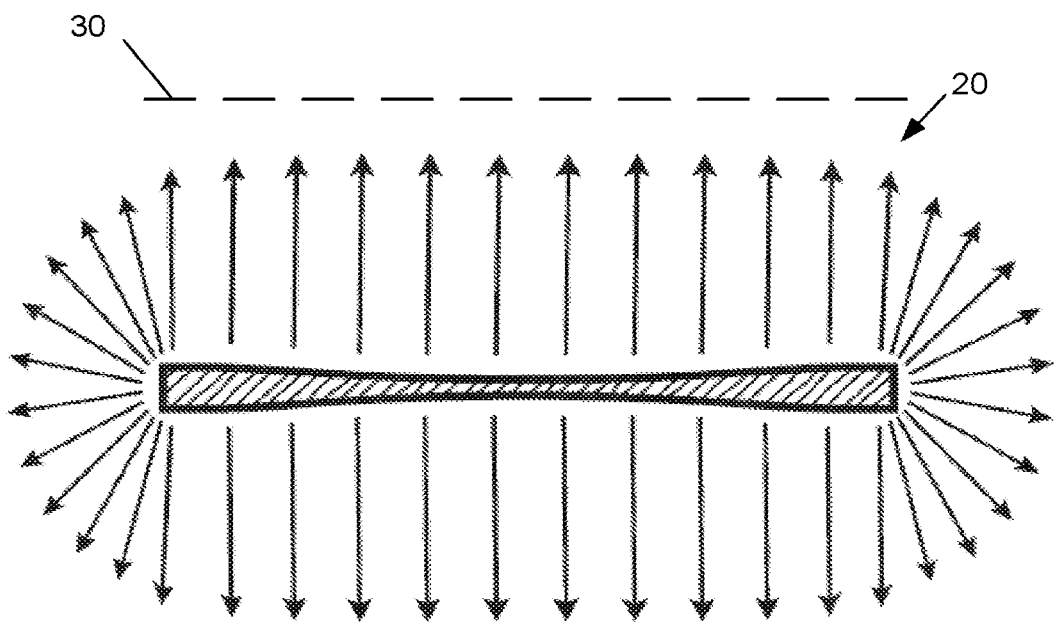
FIG. 1F illustrates a disc-like geometry for a radioactive source having a non-uniform mass across its area that may produce a more uniform radiation/dose distribution profile.

Referring now to FIG. 1E, this figure illustrates a disc-like geometry for a radioactive source 20 having a uniform mass across its area that may produce a centrally biased radiation/dose distribution profile 35. Meanwhile, FIG. 1F illustrates a disc-like geometry for a radioactive source 20 having a non-uniform mass across its area that may produce a more uniform radiation/dose distribution profile 35. In a general case, by varying the distribution of mass in selectively non-uniform patterns across the area of the source 20, one can create a dose distribution profile 35 that is tailored to the specific, desired dosage pattern in a treatment situation that requires greater dose delivery in one portion of the treatment volume versus that in others.

FIGS. 2A-2E show radionuclide source 20 with various perforation sizes and patterns which affects the dose profile 35. Other patterns and perimeter shapes, beyond those illustrated, may be used as well as understood by one of ordinary skill in the art.

Figure 2A:
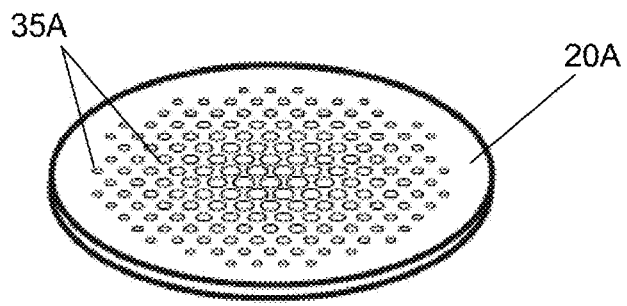
FIG. 2A shows a radionuclide source with a first set of perforation sizes and patterns which affects the radiation dose profile.

Specifically, FIG. 2A shows the radionuclide source 20A with a series of holes/perforations 35A that may range in diameter from between about 0.05 mm and about 1.00 mm. The holes 35A are laid out in a diamond grid pattern according to this exemplary embodiment. While the holes 35A are shown to have a circular shape, other geometries for the holes 35A are possible and are within the scope of this disclosure. This holds true for the remaining embodiments illustrated in all the figures: while circular geometries 25 are shown, other geometries, like square, triangular, pentagonal, hexagonal, octagonal, etc. are possible without departing from the scope of this disclosure.

In the exemplary embodiment of FIG. 2A, holes 35A having a larger diameter may be positioned in a geometric center of the pattern while holes 35A having a smaller diameter maybe positioned at a periphery relative to the diamond grid pattern, or graduated in diameter from central to peripheral placement.

Figure 2B:
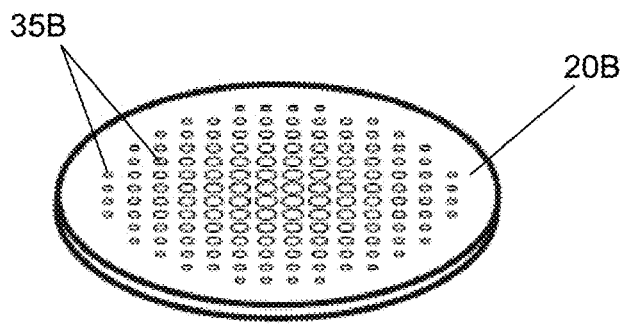
FIG. 2B shows a radionuclide source with a second set of perforation sizes and patterns which affects the radiation dose profile.

FIG. 2B shows the radionuclide source 20B with a series of holes that may range in diameter from between about 0.05 mm and about 1.00 mm. The holes 35B are laid out in a square grid pattern in which each rows and columns of the holes 35B are in parallel alignments. Similar to FIG. 2A, the larger diameter holes 35B of this exemplary embodiment of FIG. 2B may be positioned in a geometric center or central region of the square grid pattern. Meanwhile, smaller diameter holes 35B may be positioned at a periphery of the square grid pattern, or graduated in diameter from central to peripheral placement.

Figure 2C:
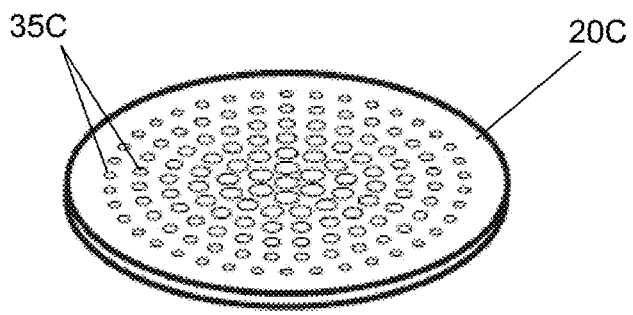
FIG. 2C shows a radionuclide source with a third set of perforation sizes and patterns which affect the radiation dose profile.

FIG. 2C shows the radionuclide source 20C with a series of holes 35C that range in diameter from between about 0.05 mm and about 1.00 mm. The holes 35C of this exemplary embodiment and are laid out in a radiating grid pattern. For this radiating grid pattern of FIG. 2C, the holes 35C may be aligned such that the holes 35C are positioned along imaginary/geometric rays that emanate/originate from a single point in the geometric center of the disc source 20C.

Similar to FIG. 2A and FIG. 2B, the larger diameter holes 35C of this exemplary embodiment of FIG. 2C may be positioned in a geometric center or central region of the radiating grid pattern. Meanwhile, smaller diameter holes 35C may be positioned at a periphery of the radiating grid pattern, or graduated in diameter from central to peripheral placement.

Figure 2D:
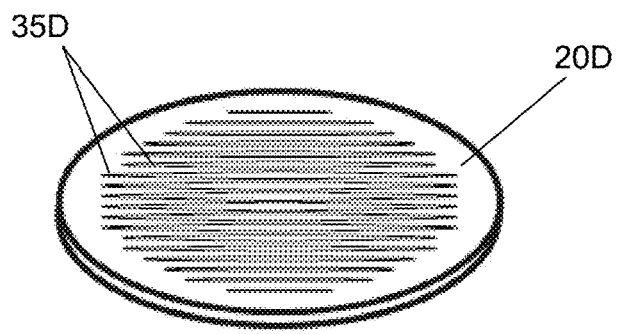
FIG. 2D shows a radionuclide source with a fourth set of perforation sizes and patterns which affects the radiation dose profile.

FIG. 2D illustrates a series of slots 35D that may range in length and may have variable width over their length and are laid out in a parallel pattern in which a length of each slot is in parallel alignment with a neighboring slot 35D. Exemplary length dimensions may range from between about 0.5 mm and about 10.0 mm. Exemplary width dimensions may range from between about 0.05 mm and about 0.50 mm.

In the exemplary embodiment illustrated in FIG. 2D, a shortest length slot 35D may be positioned at the top and bottom portion of the disc source 20D and relative to the pattern. And a few longest length slots 35D may populate a middle portion of the parallel pattern. The slots may have a taper such that their ends are narrow while their middle is broad.

Figure 2E:
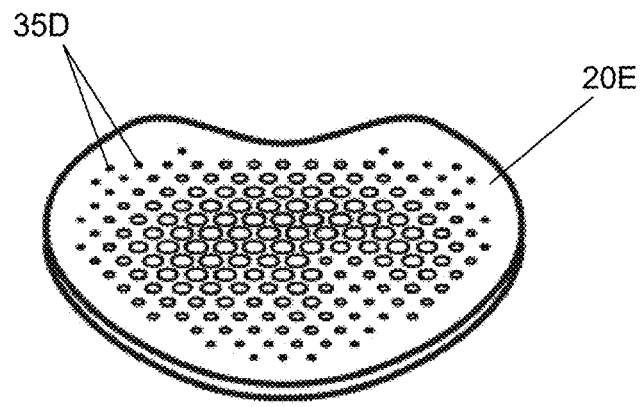
FIG. 2E shows a radionuclide source with a fifth set of perforation sizes and patterns which affects the radiation dose profile.

FIG. 2E illustrates a custom shaped source 20E with a series of variable perforations 35D in a custom/unique arrangement. The custom shaped source 20E of FIG. 2E is shown to have an irregular, curved geometry which may have some geometrical symmetry. Other irregular geometries are possible including those which may not have any lines of symmetry as understood by one of ordinary skill in the art. According to this exemplary embodiment of FIG. 2E, the perforations 35D are shown to be circular in shape. The diameters of the perforations may have ranges similar to those described in connection with FIG. 2A.

According to this exemplary embodiment of FIG. 2E, and like the embodiment of FIG. 2A, the larger diameter holes 35D may be positioned in a geometric center or central region of the custom pattern. Meanwhile, smaller diameter holes 35D may be positioned at a periphery of the custom grid pattern. As understood by one of ordinary skill in the art, any of the perforation approaches shown in FIG. 2A through FIG. 2D could be utilized in this asymmetric variable design.

Figure 3:
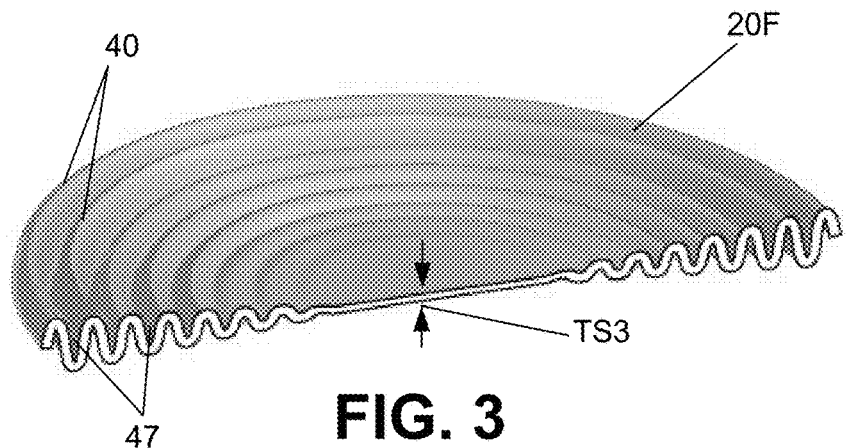
FIG. 3 illustrates a radionuclide source that has a uniform skin thickness but has surface deformations/folds that may affect/impact an amount of material per unit volume.

FIG. 3 shows a radionuclide source 20F that has a uniform skin thickness TS3 but has surface deformations/folds 40 that may affect/impact an amount of material per unit volume. These deformations/folds 40 may affect the dose profile 35. The deformations 40 may form channels 47 which may have a cross-sectional sinusoidal or v-shape. The channels 47 may have a depth that ranges from about 0.1 mm to about 1.5 mm.

The depth of the deformations may increase at a periphery of the source 20F while they decrease towards the geometric center of the source 20F. Stated differently, in this exemplary embodiment of FIG. 3, the disc 20F has a pattern of concentric folds 40 that increase (or decrease) in height from the center towards the edge of the disc 20F.

(2) Ways for Shaping Radionuclide Source Materials in an Additive or Molded Manufacturing Process (shown encapsulated within a container 25)

Figure 4A:
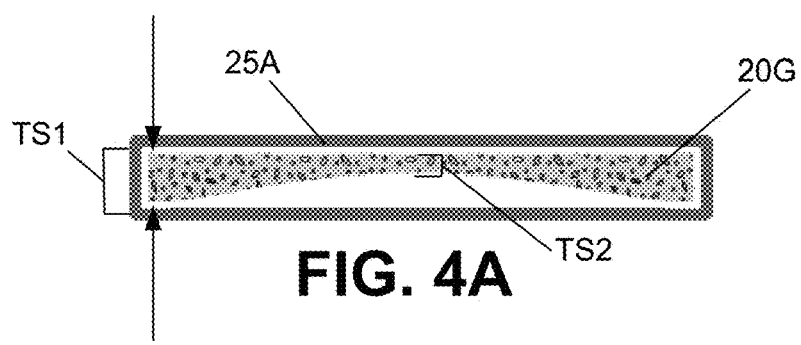
FIG. 4A shows a shape regulated matrix core material with radionuclide particles uniformly distributed in matrix.

FIG. 4A shows a shape regulated matrix core material 20G with radionuclide particles uniformly distributed in matrix. FIG. 4A also shows a simple capsule 25A having a cylindrical shape that encapsulates the shaped core 20G. The shaped core 20G may have edge thicknesses TS1 and a central thickness TS2 which may be similar to those described above in connection with FIG. 1C. Each capsule/container 25 of FIGS. 4A-4D may have a thickness between about 0.5 mm and about 2.0 mm.

Figure 4B:
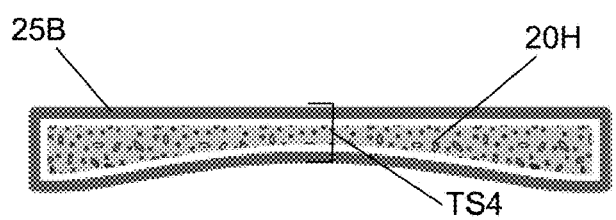
FIG. 4B shows a shaped capsule with a matching core (matching geometry) which could result from being formed by using the capsule as a mold for the matrix core material.

FIG. 4B shows a shaped capsule 25B with a matching core 20H (matching geometry) which could result from being formed by using the capsule 25B as a mold for the matrix core material. The central thickness dimension TS4 of this exemplary embodiment may have a magnitude between about 0.5 mm and about 2.0 mm.

Figure 4C:
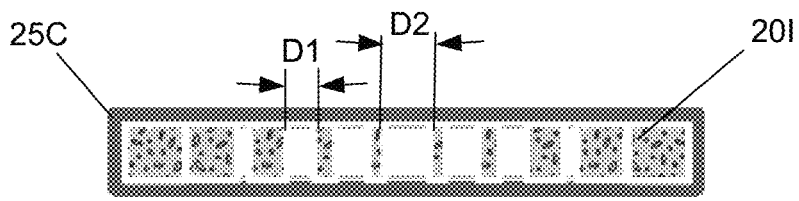
FIG. 4C shows a capsule with a perforated matrix core where perforations may have a cylindrical shape with various diameters.

FIG. 4C shows a capsule 25C with a perforated matrix core 20I. In this exemplary embodiment, the perforations may have a cylindrical shape with various diameters D1, D2. The smallest diameter D1 may have a magnitude of about 0.05 mm, while the largest diameter D2 may have a magnitude of about 1.00 mm.

Figure 4D:
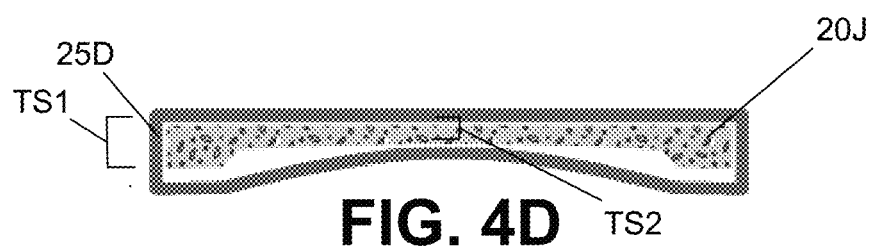
FIG. 4D shows a shaped capsule with a non-matching core where the capsule shape maintains the source position within the capsule.

FIG. 4D shows a shaped capsule 25D with a non-matching core 20J where the capsule shape maintains the source position within the capsule 25D. The shaped core 20J may have edge thicknesses TS1 and a central thickness TS2 which may be similar to those described above in connection with FIG. 1C.

Figure 4E:
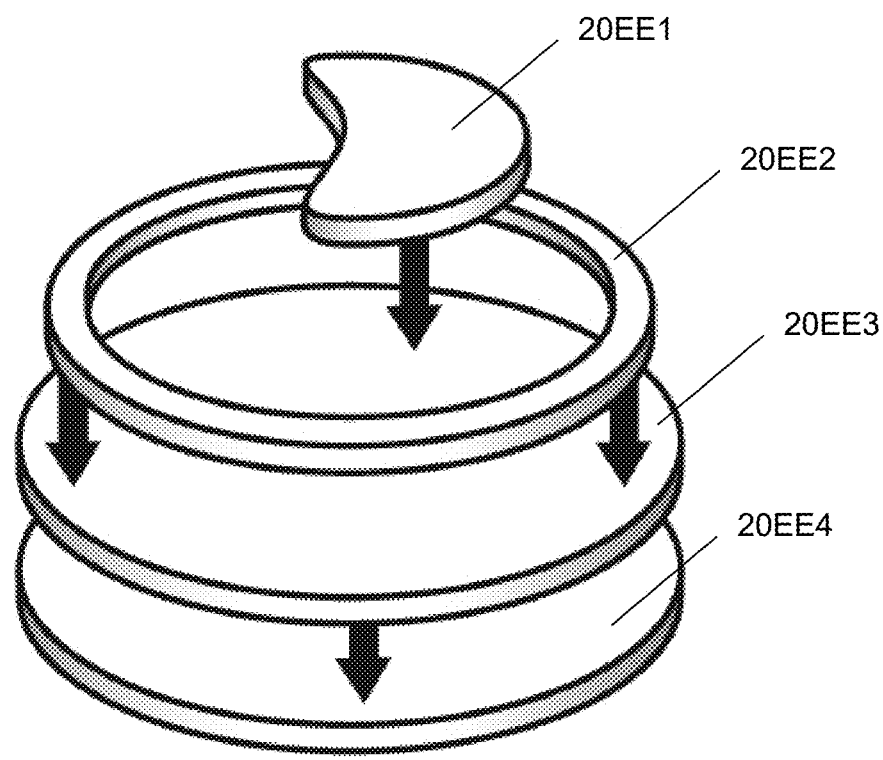
FIG. 4E illustrates a configuration of a radionuclide source where layers of radionuclide source material having either the same or differing perimeter profiles relative to each other.

FIG. 4E illustrates a configuration of a radionuclide source where layers of radionuclide source material having either the same or differing perimeter profiles relative to each other. In this exemplary embodiment, four different layers 20EE1, 20EE2, 20EE3, and 20EE4 are provided. The first layer 20EE1 has a sector shape/geometry while the second layer 20EE2 may comprise a thin ring geometry. The third layer 20EE3 and fourth layer 20EE4 may comprise a disc geometry similar to the other disc geometries previously described. The arrows indicate a sequence in which each layer 20EE is coupled to the next.

Figure 4F:
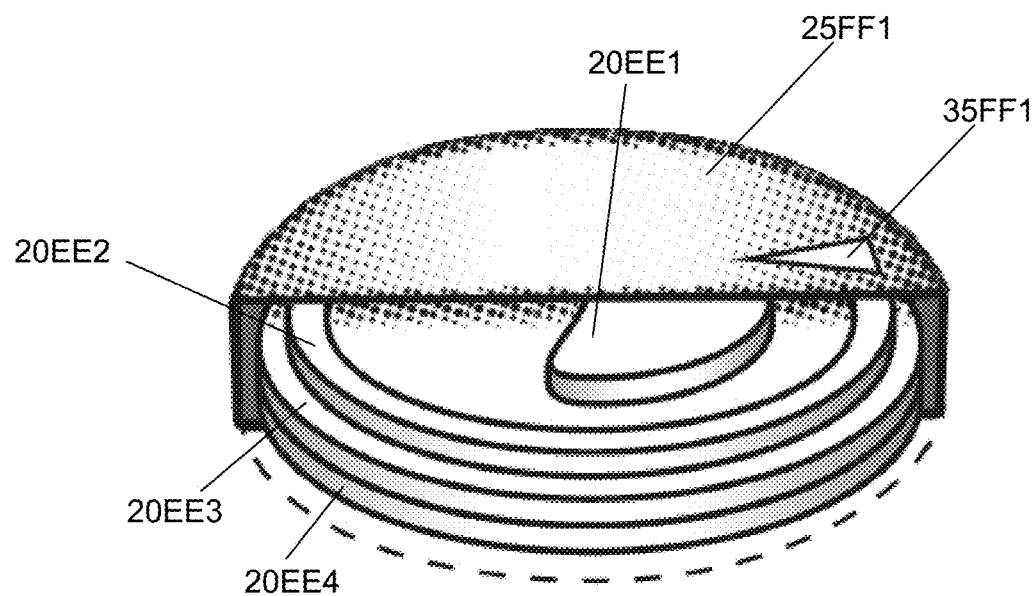
FIG. 4F illustrates the four layers of FIG. 4E that are assembled and housed in an encapsulation/container (shown partially cut away) or atop a substrate to effect a specific radiation output profile or level.

Referring now to FIG. 4F, this figure illustrates the four layers of FIG. 4E that are assembled and housed in an encapsulation/container 25 (shown partially cut away) or atop a substrate to effect a specific radiation output profile or level. As illustrated in FIG. 4F, the first layer 20EE1 is positioned within the second layer 20EE2 since the second layer 20EE2 has a ring-shape. Both the first layer 20EE1 and second layer 20EE2 rest upon the third layer 20EE3 which has a disc shape/geometry.

The container 25 may further comprise an orientation marker 35FF1 having a triangular shape in this exemplary embodiment. The orientation marker 35FF1 provides the medical practitioner with guidance as to the placement of the variable output pattern of the radionuclide source 20. Other marker types and configurations for orientation marker 35FF1 are possible and are included within the scope of this disclosure. These markers 35FF1 may be applied by one or more known methods including, but not limited to, painting, etching, laser marking, debossing, and/or embossing, etc.

The three layers 20EE1, 20EE2, 20EE3 may each have uniquely sized perimeters as well as geometries. Thus, each layer 20EE may have a different surface topography which may change each layer's respective mass pattern to effect asymmetric absorption of energy when activated in a reactor. Geometry of each layer 20EE and the distance of each layer 20EE to the anterior surface of the container 25FF1 may create unique and customized radiation patterns.

Figure 4G:
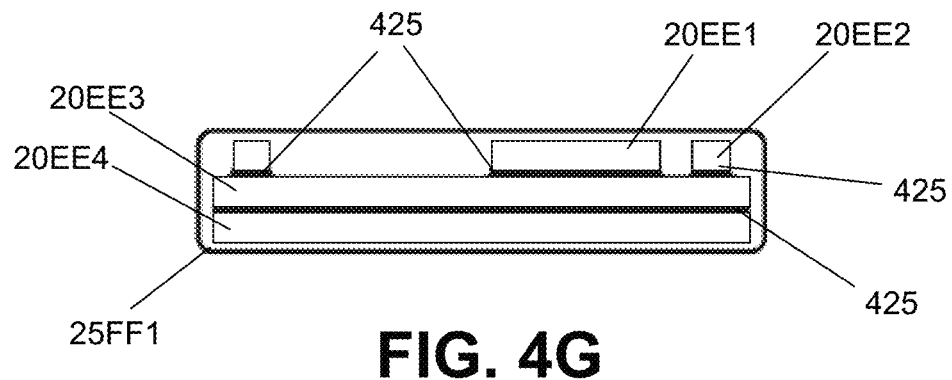
FIG. 4G illustrates a cross-sectional view of how the layers of the radionuclide source material of FIGS. 4E-4F and 4J-4H may be coupled together with an adhesive such as glue.

Referring now to FIG. 4G, this figure illustrates a cross-sectional view of how the layers of the radionuclide source material 20EE of FIGS. 4E-4F may be coupled together with an adhesive 425, such as glue. As shown in FIG. 4E, the fourth, bottom layer 20EE4 may be placed down on a surface. Next, the third layer 20EE3 may be coupled to the fourth layer 20EE4 by the adhesive 425. Subsequently, the second layer 20EE2 having the ring-shape/geometry may be placed on top of the third layer 20EE3 and coupled to the third layer 20EE3 with the adhesive 425. The first layer 20EE1 having the sector-shape/geometry may then be positioned on top of the third layer 20EE3 and within the second layer 20EE2 and coupled to the third layer 20EE3 with the adhesive 425. The coupled layers 20EE of the radionuclide source material may then be positioned within the container 25FF1. Container 25FF1 may take the form of an of the container 25 described in this disclosure.

Figure 4H:
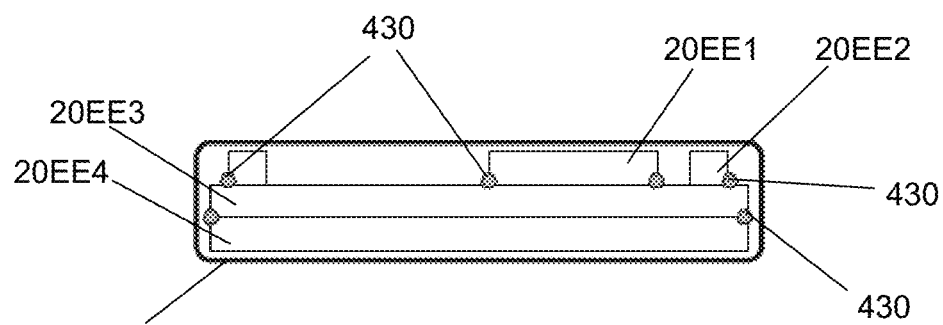
FIG. 4H illustrates a cross-sectional view of the layers of the radionuclide source material of FIGS. 4E-4F and 4J-4H which may be coupled together by welding methods, such as spot welding or laser welding.

Referring now to FIG. 4H, this figure illustrates a cross-sectional view of how the layers of the radionuclide source material 20EE of FIGS. 4E-4F may be coupled together with welds 403 via spot welding or laser welding. As shown in FIG. 4E, the fourth, bottom layer 20EE4 may be placed down on a surface. Next, the third layer 20EE3 may be coupled to the fourth layer 20EE4 by a weld 430. Subsequently, the second layer 20EE2 having the ring-shape/geometry may be placed on top of the third layer 20EE3 and secured to the third layer 20EE3 by a weld 430.

The first layer 20EE1 having the sector-shape/geometry may then be positioned on top of the third layer 20EE3 and within the second layer 20EE2 and coupled to the third layer 20EE3 with a weld 430. The coupled layers 20EE of the radionuclide source material may then be positioned within the container 25FF1. Container 25FF1 may take the form of any of the containers 25 described in this disclosure.

Figure 4I:
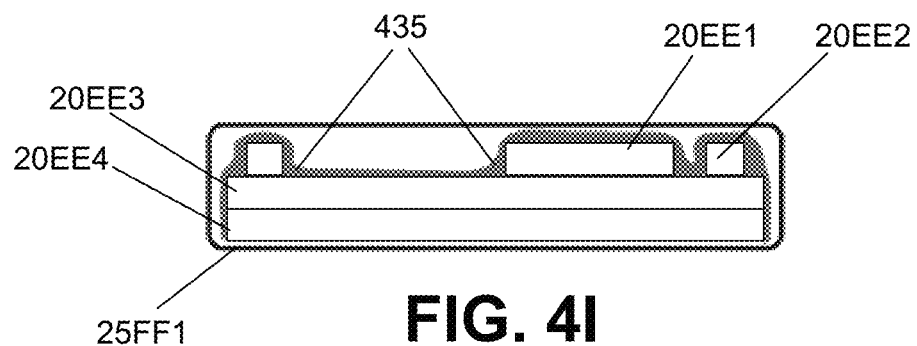
FIG. 4I illustrates a cross-sectional view of how the layers of the radionuclide source material of FIGS. 4E-4F and 4J-4H may be coupled together with a potting material.

Referring now to FIG. 4I, this figure illustrates a cross-sectional view of how the layers of the radionuclide source material 20EE of FIGS. 4E-4F may be coupled together with a potting material 435. The potting material may comprise thermosetting plastics and silicone rubber gels, which may include, but are not limited to, polyurethane, silicone, and epoxy. In the potting process, the potting material 435 is applied as an insulating liquid compound that hardens, permanently protecting the layers 20EE.

As shown in FIG. 4E, the fourth, bottom layer 20EE4 may be placed down on a surface. Next, the third layer 20EE3 may be positioned on the fourth layer 20EE4. Subsequently, the second layer 20EE2 having the ring-shape/geometry may be placed on top of the third layer 20EE3. The first layer 20EE1 having the sector-shape/geometry may then be positioned on top of the third layer 20EE3 and within the second layer 20EE2. Next, the layers 20EE are all coupled together by the potting material 435 which may be applied as an insulating liquid which later hardens. The coupled layers 20EE of the radionuclide source material may then be positioned within the container 25FF1. Container 25FF1 may take the form of any of the containers 25 described in this disclosure.

Figure 4J:
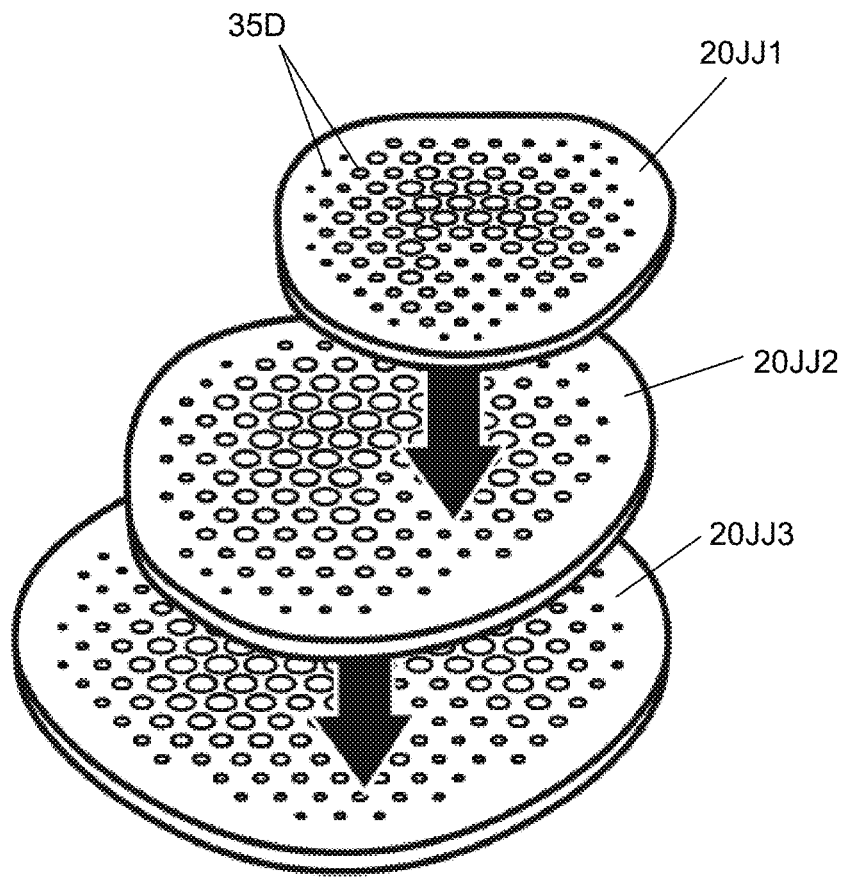
FIG. 4J illustrates a configuration where layers of radionuclide source material may have either the same or differing perimeter profiles and radiation emission control/focusing features relative to each other.

Referring now to FIG. 4J, this figure shows a configuration where layers 20JJ of radionuclide source material may have either the same or differing perimeter profiles and features relative to each other. Specifically, each layer 20JJ may have options of the previously described features such as, but not limited to perforations/holes 35, selective sectional thickness variations, and/or variable surface contours to affect each layer's local output of radiation. In the exemplary embodiment illustrated in FIG. 4J, three layers 20JJ1, 20JJ2, 20JJ3 are depicted. Each layer 20JJ may have holes 35 where each layer 20JJ has holes 35 having varying diameters, similar to those described above and illustrated in connection with FIG. 2E.

Figure 4K:
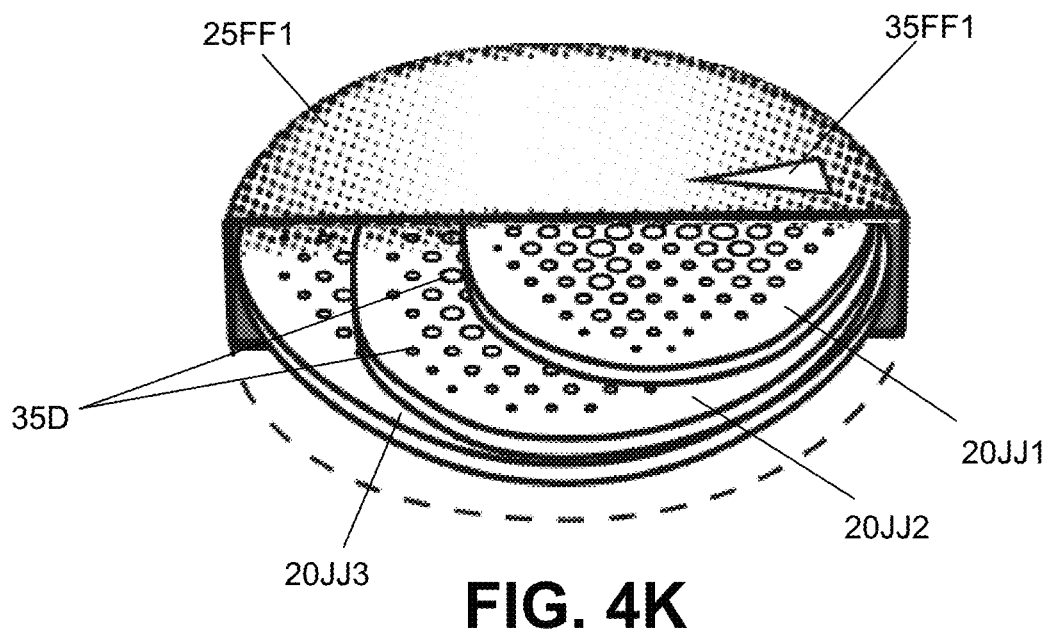
FIG. 4K illustrates the layers of radionuclide source material of FIG. 4J assembled together and contained within a housing.

Referring now to FIG. 4K, this figure illustrates the layers 20JJ of FIG. 4J assembled together and contained within a housing 25FF1. The housing 25FF1 is shown partially cut away. Container 25FF1 may take the form of any of the containers 25 described in this disclosure. The container 25FF1 may further comprise an orientation marker 35FF1, which has been previously described in connection with FIG. FIG. 4F above.

The three layers 20JJ1, 20JJ2, 20JJ3 may each have uniquely sized perimeters and geometries, as well as thicknesses. Further the patterns for the aperture 35 in each layer 20JJ may be unique or similar relative to another layer 20JJ. Thus, each layer 20JJ may have a different surface topography, and/or pattern of apertures 35 which may change each layer's respective mass pattern to effect asymmetric absorption of energy when activated in a reactor. Geometry of each layer 20JJ and the distance of each layer 20JJ to the anterior surface of the container 25 may create unique and customized radiation patterns.

Figure 5A:
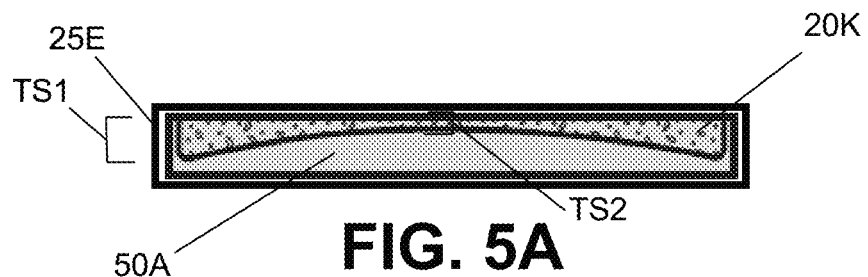
FIG. 5A shows a shaped substrate with molded or poured source material.

FIGS. 5A-5D show composite sources 20, both with and without a substrate material 50, with various methods of formation. Specifically, FIG. 5A shows a shaped substrate 50A with molded or poured source material 20K. The shaped source material 20K may have edge thicknesses TS1 and a central thickness TS2 which may be similar to those described above in connection with FIG. 1C. The areas/regions of the substrate 50A [and for the other embodiments of FIGS. 5B-5D] which do not have the source material may be made of a polymeric material, a ceramic or other moldable compound material as understood by one of ordinary skill in the art.

Polymeric materials, as understood by one of ordinary skill in the art, can be grouped into three general categories: 1) thermoplastics; 2) thermosets; and 3) elastomers. Thermoplastics can be softened and re-hardened indefinitely, as often as they are reheated providing the temperature is not high enough as to cause decomposition. Thermoplastics have linear or branched molecular chain structures with few links, if any between chains. Typical examples include nylon, polyethylene, polycarbonate, and polyvinyl chloride (PVC).

Meanwhile, thermoset polymers are rigid and not softened by the application of heat. Such polymers have molecular structures which are extensively cross-linked. Because of this, when heat causes the bonds to break, the effect is not reversible on cooling. Typical examples of thermoset polymers include, but are not limited to, phenolics, epoxies and resins.

Elastomers are polymers which as a result of their molecular structure allow considerable elastic behavior. Such materials are lightly cross-linked polymers. Between the cross-links the molecular chains are fairly free to move. Elastomers may include, but are not limited to, rubber, silicone, and polyurethane.

Figure 5B:
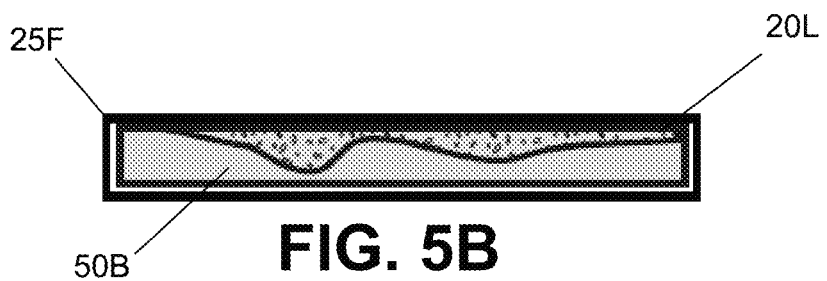
FIG. 5B shows a custom shaped substrate with molded or poured source material.

FIG. 5B shows a custom shaped substrate 50B with molded or poured source material 20L. According to this exemplary embodiment, the source material 20K may have an irregular geometry which is not symmetrical. However, irregular geometries which have one or more lines of symmetry are possible and are within the scope of this disclosure.

Figure 5C:
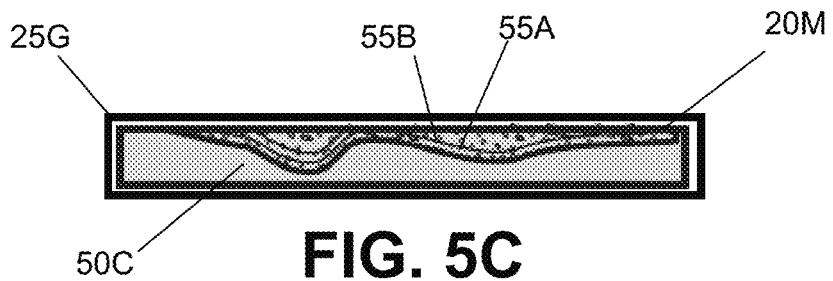
FIG. 5C shows an additive application of source material on a substrate as indicated by the sequence of curved lines forming the source material.

FIG. 5C shows an additive application of source material 20M on a substrate 50C as indicated by the sequence of curved lines 55A, 55B forming the source material 20M.

Figure 5D:
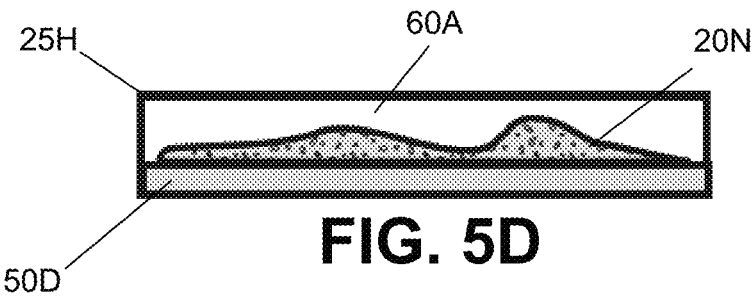
FIG. 5D shows a selectively built-up coating of source material on a substrate.

FIG. 5D shows a selectively built-up coating of source material 20N on a substrate 50D. Either generic regular/symmetrical or custom/irregular profiles/cross-sections are possible, where encapsulation is also shown by either a molded or poured encapsulating material such as a polymer, ceramic or other moldable compound 60A, or by an outer encapsulating container.

Figure 5E:
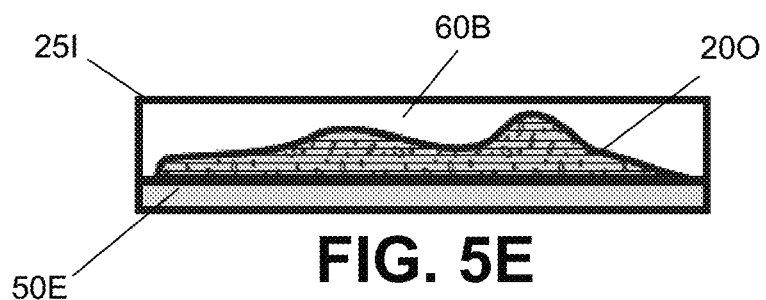
FIG. 5E shows a 3D printed source material on a substrate with encapsulation shown by either a molded or poured encapsulating material such as a polymer, ceramic or other moldable compound, or by an outer encapsulating container.

FIG. 5E shows a 3D printed source material 20-O on substrate 50E with encapsulation shown by either a molded or poured encapsulating material such as a polymer, ceramic or other moldable compound 60B, or by an outer encapsulating container 25I.

Figure 5F:
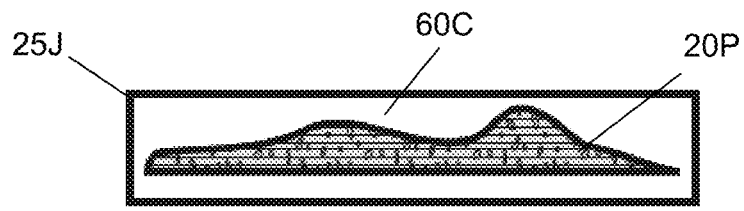
FIG. 5F shows a 3D printed source material with no substrate and in encapsulation (potted) by either a molded or poured encapsulating material such as a polymer, ceramic or other moldable compound, or by being placed within an outer encapsulating container.

FIG. 5F shows a 3D printed source material 20P with no substrate and in encapsulation (potted) by either a molded or poured encapsulating material such as a polymer, ceramic or other moldable compound 60C, or by being placed within an outer encapsulating container 25J. The source material 20P may be centrally placed in potting material or adhered if in a capsule.

Figures 6A, 6B:
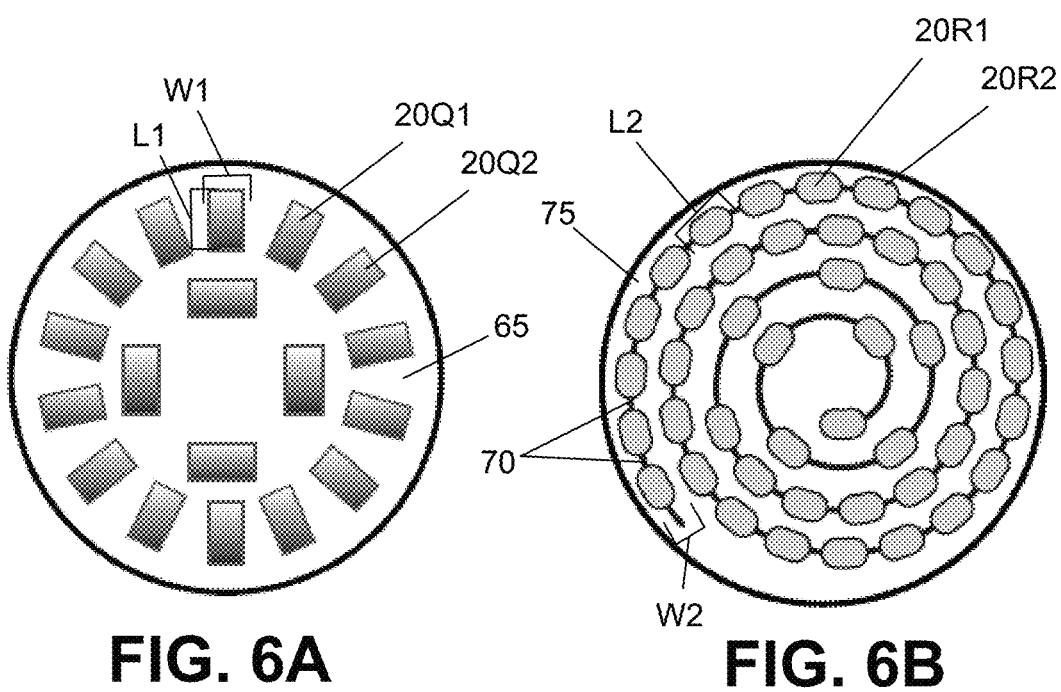
FIG. 6A shows controlled spacing of radioactive seeds in a molded carrier.
FIG. 6B shows selectively arranged radioactive beads on a wire or string, spaced and coiled to derive the desired dosage profile.

FIGS. 6A-6D show other carrier methods used in conjunction with beads, seeds, and microspheres to form the desired dose profile 35. Specifically, FIG. 6A shows controlled spacing of radioactive seeds 20Q in a molded carrier 65. Each seed 20Q may have length dimension L1 which has a magnitude that ranges between about 1.0 mm to about 20.0 mm. Each seed 20Q may have width dimension W1 which has a magnitude that ranges between about 0.8 mm to about 4.0 mm. The seeds 20Q may be secured to a carrier/encapsulation 65. The carrier/encapsulation 65 may be the same as in FIG. 5F discussed above.

FIG. 6B shows radioactive beads 20R on a wire or string 70, spaced and coiled to derive the desired dosage profile. Each bead 20R may have length dimension L2 which has a magnitude that ranges between about 0.02 mm to about 5.0 mm. Each bead 20R may have width dimension W2 which has a magnitude that ranges between about 0.02 mm to about 5.0 mm. The beads 20R may be secured to a carrier/encapsulation 75. Carrier/encapsulation 75 may be formed as similarly described and as illustrated in FIG. 5F discussed above.

FIG. 6C shows radioactive microspheres S in a polymer matrix 75 with activity/dose 35 controlled by a molded thickness as illustrated in FIG. 6D. As illustrated in FIG. 6D, the polymer matrix 20K may have edge thicknesses TS1 and a central thickness TS2 which may be similar to those described above in connection with FIG. 1C. The microspheres S may have diameters which range from between about 0.2 mm and about 2.0 mm. The biocompatible resin microspheres S containing yttrium-90 have a median diameter of about 32.5 microns (a range between about 20.0 and 60.0 microns). Yttrium-90 is a high-energy beta-emitting isotope with no primary gamma emission. The maximum energy of the beta particles is usually about 2.27 MeV with a mean of about 0.93 MeV. Materials could include epoxies, PMMA, polyesters and copolyesters and other materials of suitable structural strength, biocompatibility and radiation resistance.

FIG. 7 shows a capsule 25 used for encapsulating radionuclide source materials (not shown). The capsule 25 may have dimensions described above in connection with FIGS. 4-5. This thin-walled encapsulation 25 could be made from metals, polymers, ceramics or glass. In another exemplary embodiment the encapsulation 25 may comprise a material which is poured or molded so as to wholly or partially surround or pot the source 20 (not shown) with encapsulating material 25. Exemplary materials for capsule 25 may include, but are not limited to, any one or a combination of titanium, gold, silver, steel, copper, and acrylic.

FIGS. 8A-8E illustrate manufacturing methods for source encapsulation housings 25. Bonding between the components illustrated in FIGS. 8A-8E may accomplished by welding, sealing, crimping, or any combination thereof. The housings/capsules 25 of FIGS. 8A-8E may have dimensions as previously described for the earlier exemplary embodiments.

Specifically, FIG. 8A shows a three-piece assembly capsule 25 which includes a lid 800, perimeter wall 804 and substantially flat bottom 802. Once assembled, this three-piece capsule 25 may hold any one of the radioactive sources 20 described previously and illustrated in the Figures of this disclosure.

FIG. 8B illustrates a two-piece capsule 25 that comprises a lid 800 which is attached to a bottom 806 with an integral wall that is either a stamped formed element or a machined element. Once assembled, this two-piece capsule 25 may hold any one of the radioactive sources 20 described previously and illustrated in the Figures of this disclosure.

Figure 8C:
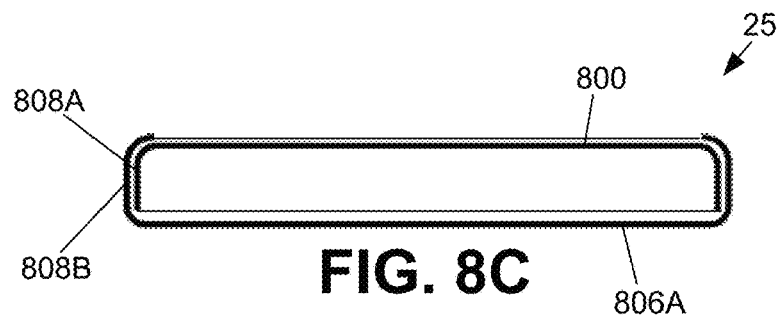
FIG. 8C illustrates a lid which has its own integral side wall and which is positioned within a bottom.
Figure 8D:
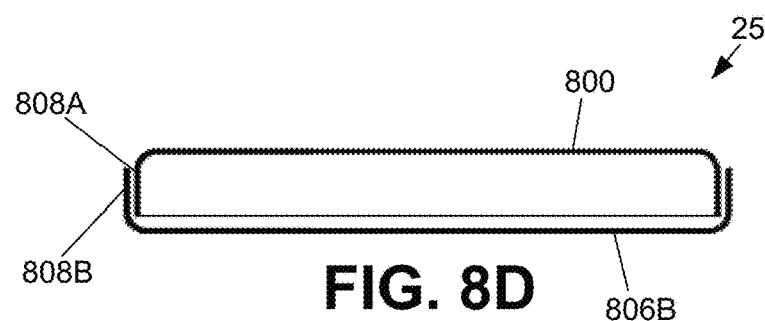
FIG. 8D illustrates an exemplary embodiment similar to FIG. 8C except that the integral side wall of the bottom may have a height which does not completely surround/encapsulate a height dimension for the integral side wall of the lid.

FIGS. 8C-8D show configurations with two nested capsule halves 800-806, welded, sealed, or crimped together to form a capsule 25. Specifically, FIG. 8C illustrates a lid 800 which has its own integral side wall 808A which is positioned within a bottom 806A. The bottom 806A of FIG. 8C has its own integral side wall 808B which encapsulates/surrounds the integral side wall of the lid 800. The integral side wall 808B of the bottom 806 may have a height which completely surrounds/encapsulates [is greater than] a height dimension for the integral side wall 808A of the lid 800.

FIG. 8D illustrates an exemplary embodiment similar to FIG. 8C except that the integral side wall 808B of the bottom 806 may have a height which does not completely surround/encapsulate [is less than or equal to] a height dimension for the integral side wall 808A of the lid 800.

Figure 8E:
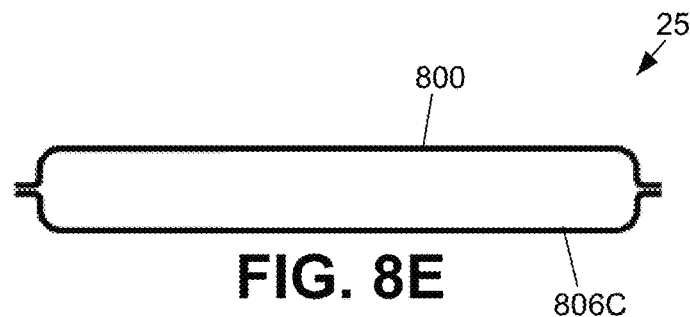
FIG. 8E illustrates a clamshell configuration having a lid and bottom suitable for welding.

FIG. 8E illustrates a clamshell configuration having a lid 800 and bottom 806C suitable for welding. According to this exemplary embodiment, the lid 800 and bottom 806C may have symmetrical geometries relative to one another. That is, the lid 800 may have a geometry which is a mirror image of the bottom 806C. However, other exemplary embodiments are possible in which the geometries of the lid 800 and bottom 806 are not identical, similar to FIGS. 8A-8D, and which may be suitable for welding.

FIGS. 9A-9E show examples of various assembly methods for encapsulation to form a capsule/housing 25 using non-metallic materials. Other material combinations are also possible, such as metal/glass, metals/polymers combinations, etc. The housings/capsules 25 of FIGS. 9A-9E may have dimensions as previously described for the earlier exemplary embodiments. The capsule 25 may encapsulate any of the radioactive sources 20 previously described and illustrated.

Figure 9A:
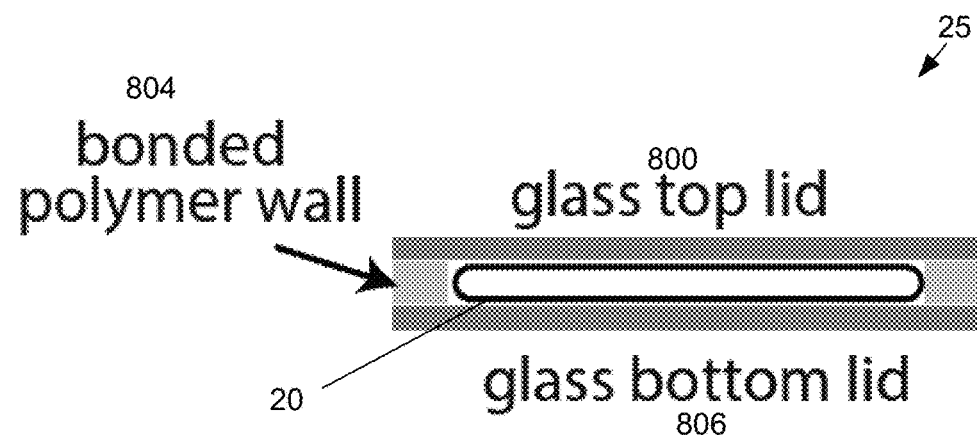
FIG. 9A illustrates a glass lid and glass bottom bonded to a polymer wall.

Specifically, FIG. 9A illustrates a glass lid 800 and glass bottom 806 bonded to a polymer wall 804. Exemplary polymers for polymer wall 804 include, but are not limited to epoxies, Polymethyl methacrylate (PMMA), Polyesters and copolyesters and other materials of suitable structural strength, biocompatibility and radiation resistance.

Figure 9B:
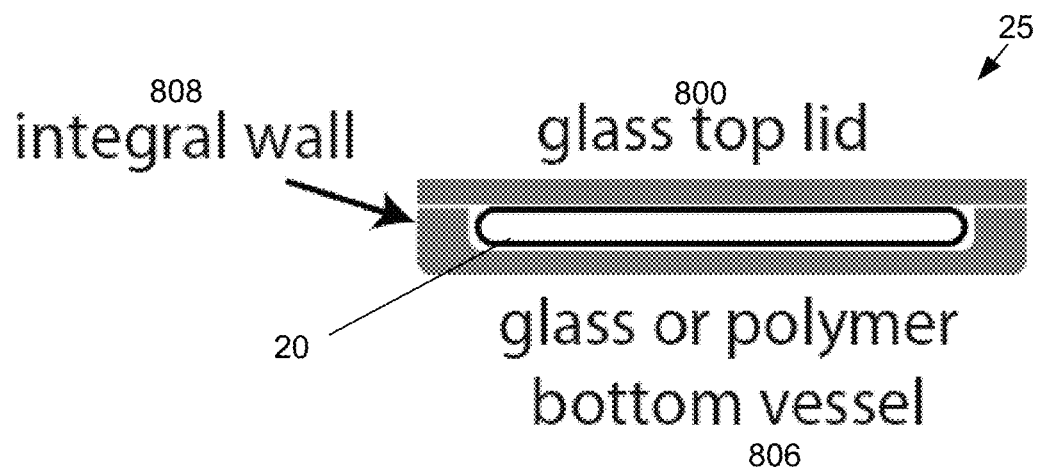
FIG. 9B shows a glass lid bonded to a glass bottom with an integral sidewall.
Figure 9C:
FIG. 9C illustrates a poured or molded encapsulation surrounding any source core type described here.

FIG. 9B shows a glass lid 800 bonded to a glass bottom 806 with an integral sidewall 808. FIG. 9C illustrates a poured or molded encapsulation 900 surrounding any source core type described here. The encapsulation 900 may include one or more of the following materials: epoxies, PMMA, Polyesters and copolyesters and other materials of suitable structural strength, biocompatibility and radiation resistance.

Figure 9D:
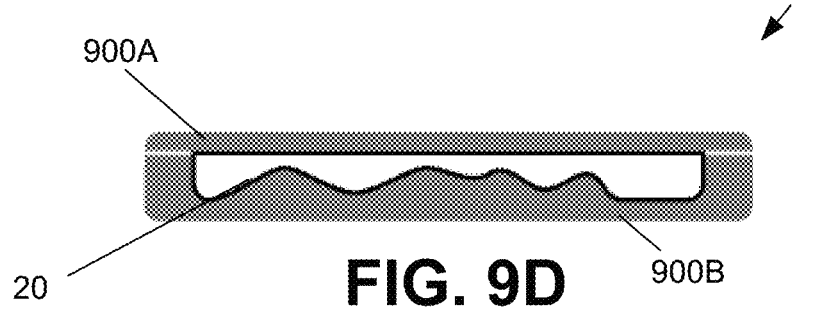
FIG. 9D illustrates encapsulations forming a capsule which has an irregular, non-repeating, non-geometrical protrusions.
Figure 9E:
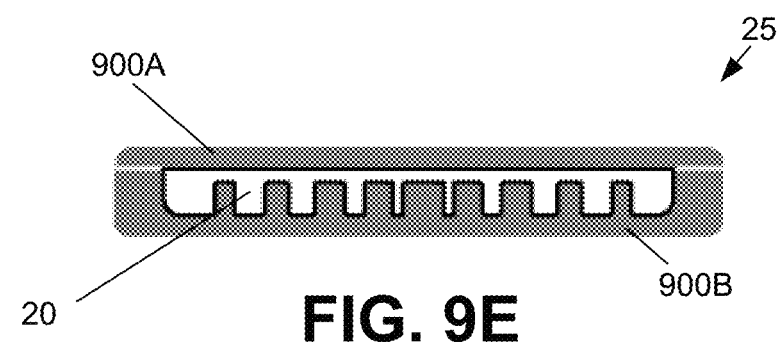
FIG. 9E illustrates encapsulations forming a capsule which has regular, repeating, and simple geometry type protrusions.

FIGS. 9D-9E shows encapsulations 900A-B, 900C-D with variable thickness or protruding inner features. Such shaping could serve simply to hold the source or to act as a defacto mold for poured or injected radionuclide source materials, thus inducing a desired shape variation to the source 20. This would provide a positionally controllable activity level resulting from the source thickness profile.

Specifically, FIG. 9D illustrates encapsulations 900A-B forming a capsule 25 which has an irregular, non-repeating, non-geometrical protrusions. Meanwhile, FIG. 9E illustrates encapsulations 900C-D forming a capsule 25 which has regular, repeating, and simple geometry type protrusions.

Figure 10A:
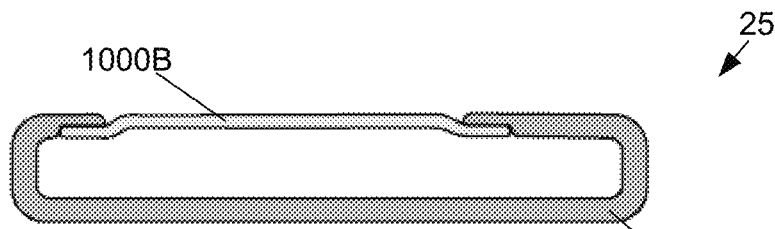
FIG. 10A illustrates a metal encapsulation where a secondary metal section having a different shielding capability relative to a primary metal section has been added to the capsule.
Figure 10B:
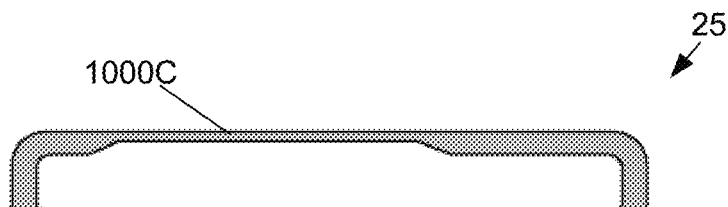
FIG. 10B shows a metal encapsulation where a section has been made thinner to allow greater radiation levels to be allowed through the wall of the capsule relative to the remaining section of the wall.
Figure 10C:
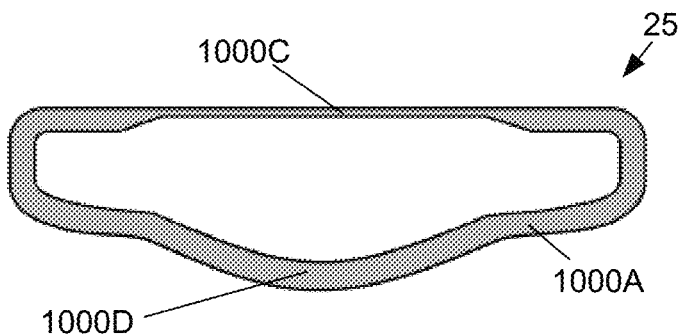
FIG. 10C illustrates a metal encapsulation where a section has been shaped to focus radiation in a particular direction.

FIGS. 10A-10C show several configurations of metallic enclosures 25 wherein control of radiation emissions are implemented. The housings/capsules 25 of FIGS. 10A-10C may have dimensions as previously described for the earlier exemplary embodiments. The capsules 25 of FIGS. 10A-10C may encapsulate any of the radioactive sources 20 [not shown in these figures] but were previously described above and illustrated.

FIG. 10A illustrates a metal encapsulation 25 where a secondary metal section 1000B having a different shielding capability relative to a primary metal section 1000A has been added to the capsule 25 and affixed in a sealed manner thereto, usually by welding and/or by crimping with a chemical adhesive as understood by one of ordinary skill in the art.

FIG. 10B shows a metal encapsulation 25 where a section 1000C has been made thinner to allow greater radiation levels to be allowed through the wall of the capsule 25 relative to the remaining section 1000A of the wall. As understood by one of ordinary skill in the art, shielding radiation and a corresponding radiation attenuation amount are based on material, initial thickness, reduced thickness, shielding material, the type of radionuclide in the source, and the source activity level.

FIG. 10C illustrates a metal encapsulation 25 where a section 1000D has been shaped to focus radiation in a particular direction, or at a specific focal area that is projected through a thin section 1000C of the capsule 25. The thicknesses of this exemplary embodiment of FIG. 10C may be similar to those described above in connection with FIG. 10B.

Figure 11A:
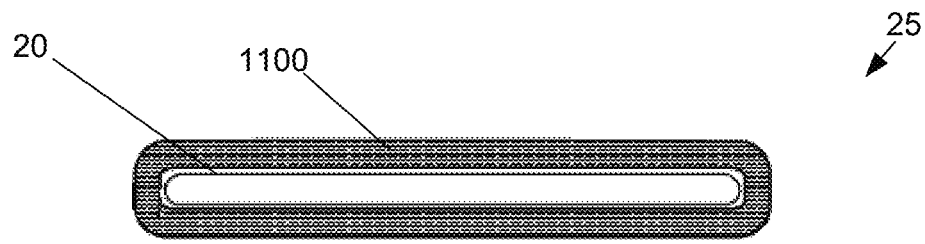
FIG. 11A shows a 3D printed encapsulation optionally with a metal, such as stainless steel, titanium or gold, or a metal impregnated compound.
Figure 11B:
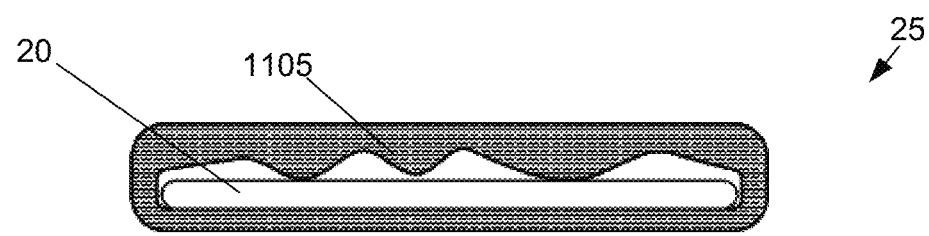
FIG. 11B shows a composite shield type of capsule where the inside of the capsule is given a contour to allow variable dose rate emissions across the face of the source within.
Figure 11C:
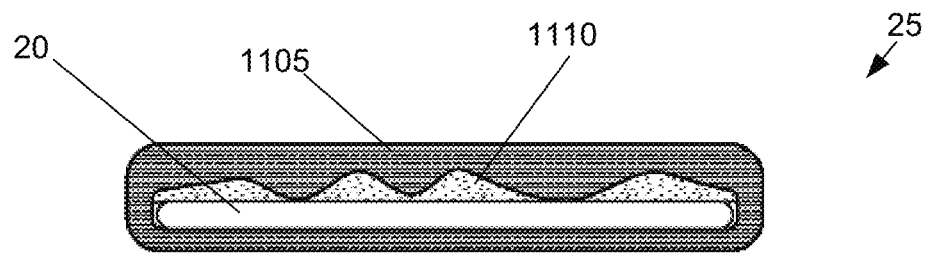
FIG. 11C shows a composite shield type of capsule where the inside of the capsule is given a contour with a secondary layer of different shielding density to allow variable shielding across the face of the source within.

FIGS. 11A-11C show several configurations for capsules 25 where several layers of a material, such as a polymer, glass or a ceramic is produced using additive/layered manufacturing methods to form the encapsulation 25. If metal-containing materials are used such as lead or tungsten, such materials may provide shielding properties relative to the radioactive source 20 contained within each capsule 25. The housings/capsules 25 of FIGS. 11A-11E may have dimensions as previously described for the earlier exemplary embodiments. The capsules 25 of FIGS. 11A-11C may encapsulate any of the radioactive sources 20 that were previously described above and illustrated.

Some of the exemplary embodiments of FIGS. 11A-11E have variable shielding features to provide further control over the type and distribution 35 [See FIG. 1A] of radiation emissions from the source 20. Compounds capable of being printed by additive means/by layers can have metal constituents added to them, allowing uniquely suited and shaped shielding for the radiation source material to be produced or "printed"/3-D printed as understood by one of ordinary skill in the art.

Exemplary compounds include, but are not limited to, finely granulated, dense metal such as tungsten, stainless steel or lead mixed into a carrier matrix such as a thermoplastic polymer such as a copolyester, Poly Cydohexylenedimethylene Terephthalate glycol (PCTG) for example, or a catalyzing reaction polymer such as an ultra-violet (UV) light initiated reaction epoxy or polyester compound.

Specifically, FIG. 11A shows a 3D printed encapsulation 25 optionally with a metal, such as stainless steel, titanium or gold, or a metal impregnated compound 1100. The compound 1100 may include, but is not limited to, finely granulated tungsten, stainless steel or lead mixed into a carrier matrix such as a thermoplastic polymer such as a copolyester, PCTG for example, or a catalyzing reaction polymer such as a UV light-initiated-reaction epoxy or polyester compound, or a ceramic or a glass.

The printed encapsulation 25 embodiment of FIGS. 11A-11E may be formed in layers using 3D printing techniques, build-up manufacturing, or other layering methods. Other layering or additive manufacturing methods that one of ordinary skill in the art can utilize, include, but are not limited to at least seven technologies listed in the ISO standards which may comprise any one and/or a combination of the following methods: binder jetting, directed energy deposition, material extrusion, material jetting, powder bed fusion, sheet lamination, and vat photopolymerization.

FIG. 11B shows a composite shield type of capsule 25 where the inside of the capsule 25 is given a contour 1105 to allow variable dose rate emissions across the face of the source 20 within. FIG. 11C shows a composite shield type of capsule where the inside of the capsule 25 is given a contour 1105 with a secondary layer 1110 of different shielding density to allow variable shielding across the face of the source 20 within. A first shielding material may comprise a low density shielding material that may include, but is not limited to, a polymer such as PMMA or a glass, while a second material may comprise a high density shielding material. The high density shielding material may include, but is not limited to, metal, (as mentioned above in reference to FIG. 11A,) infused into a polymer, glass or polymer/ceramic slurry.

Figure 11D:
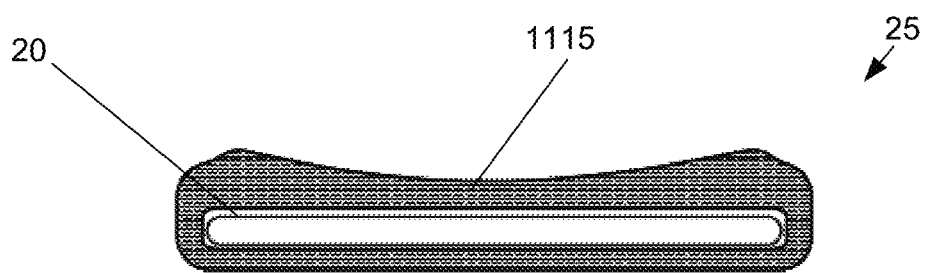
FIG. 11D illustrates a composite shield type of capsule where the outer surface is given a contour to vary the shielding across the face of the source and/or to fit against an anatomical feature.

FIG. 11D illustrates a composite shield type of capsule 25 where the outer surface 1115 is given a contour to vary the shielding across the face of the source 20 and/or to fit against an anatomical feature. This embodiment of FIG. 11D may be formed from 3D printing techniques, in a layered fashion as understood by one of ordinary skill in the art.

Figure 11E:
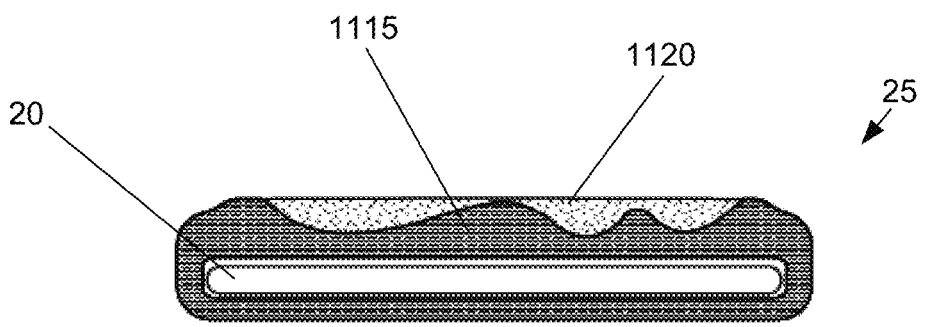
FIG. 11E shows a multi-material composite shield type of capsule to allow variable shielding across the face of the source within.

FIG. 11E shows a multi-material composite shield type of capsule 25 to allow variable shielding across the face of the source 20 within. In this exemplary embodiment, the first material 1115 enveloping the entire source 20 may comprise a high density shielding material while the second material 1120 that is deposited on the first material 1115 may comprise a low density shielding material.

The low density shielding material 1120 may comprise a polymer such as PMMA or a glass while the high density material 1115 may comprise a metal, (as mentioned above in reference to FIG. 11A,) a metal infused into a polymer, glass or polymer/ceramic slurry to be molded or built up through 3D printing techniques.

Referring now to FIGS. 12 and 13, an organ of the body, such as an eye 1205A, can grow a tumor 1210A which usually needs treatment. Placement of a radionuclide, such as the radioactive sources 20 illustrated in FIGS. 1-11 described above, in close contact with the tumor 1210A, often referred to as brachytherapy, is a widely used cancer treatment.

Figure 12A:
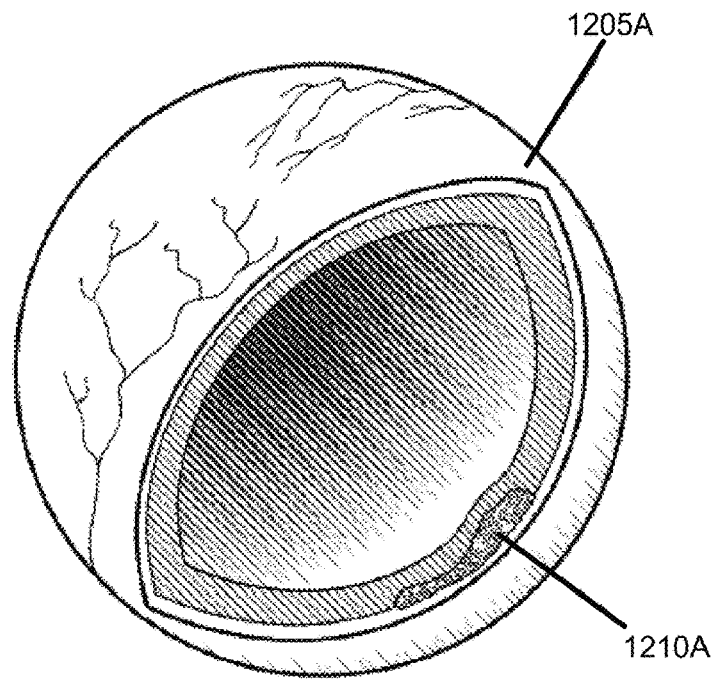
FIG. 12A illustrates a first exemplary embodiment of internal cancer of an organ, such as the eye, where an internal tumor does not distort a geometry of an outer wall of the organ.
Figure 12B:
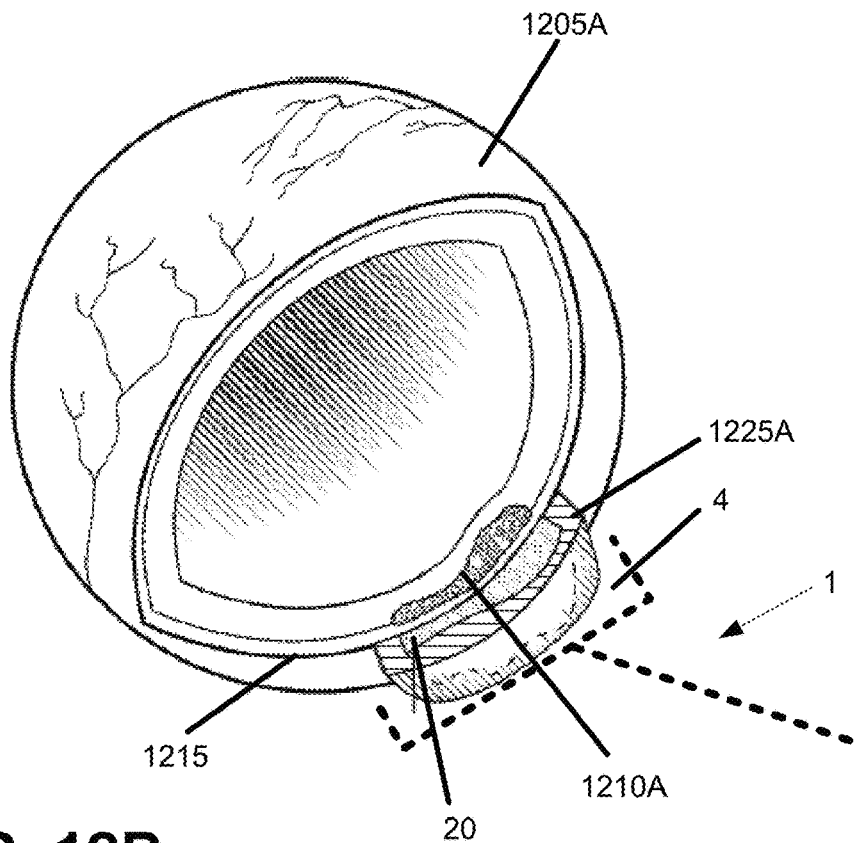
FIG. 12B illustrates a radioactive source placed adjacent to internal cancer of an organ, such as the human eye according to a first exemplary embodiment.

Here two treatment situations are illustrated: one shown in FIG. 12A-12B, where the tumor 1210A does not present a distortion of the geometry of an outer wall of the organ 1205A. The other situation illustrated in FIGS. 13A-13B is where the tumor 1210B grows outward from the surface of the organ 1205B, creating a new contour 1315 which distorts a geometry of an outer wall of the organ 1205B. As noted previously, the inventive radioactive sources 20 of FIGS. 1-13 may be included in other treatment devices for treating other organs 1205 in the human body besides the human eye.

Other organs 1205 besides the human eye, eye lids and orbit which may be treated by the inventive radioactive sources 20, may include, but are not limited to the following organs and organ systems: organs of digestion including, but not limited to, the stomach, liver, small intestine, large intestine, rectum, and anus; organs of respiration, including, but not limited to, the lungs, nose, trachea, and bronchi; organs of excretion, including, but not limited to, the kidneys, urinary bladder, and urethra; organs of circulation, including, but not limited to, the heart, blood vessels, and spleen; organs of the nervous system, including, but not limited to, the brain and spinal cord; organs of reproduction, including, but not limited to, the testis and penis in male, the uterus, ovaries & mammary glands in the female; organs of the endocrine system, including, but not limited to, the pituitary gland, adrenal, thyroid, pancreas, parathyroid, and prostate glands; organs of senses, including, but not limited to, the skin, tongue, nose, and ears; organs of the immune system, including, but not limited to, the spleen, thymus, and bone marrow; organs of metabolism, including, but not limited to, the liver, just to name a few.

Referring back to FIG. 12B, the variable strength source 20 has its outer surface geometry contoured to match the normally contoured surface 1215 of the organ 1205A while the cross sectional geometry 1230 of the source 20 may be variable in its thickness dimension and is so shaped as to provide, through its cross sectional thickness variations, a unique radiation output/emission corresponding to the treatment demands of non-uniformities present in a typical tumor 1210A. The substrate or container shell 1225A is formed to hold the radiation source material 20 and provide any necessary features for placement and/or anchoring.

Also illustrated in FIG. 12B is a medical device 1 shown with dashed lines which may comprise the cavity 4 described above in connection with FIG. 1D. The medical device 1 of FIG. 13B is a mere representation [oversimplification] of the ophthalmic treatment device 1 illustrated in FIG. 1D. However, other medical devices 1 that are used to treat other cancers and other organs as discussed above are included within the scope of this disclosure.

Figure 12C:
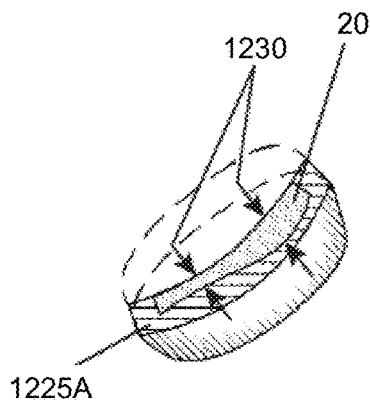
FIG. 12C illustrates a cross sectional view of the radioactive source shown in FIGS. 12A-12B.
Figure 13A:
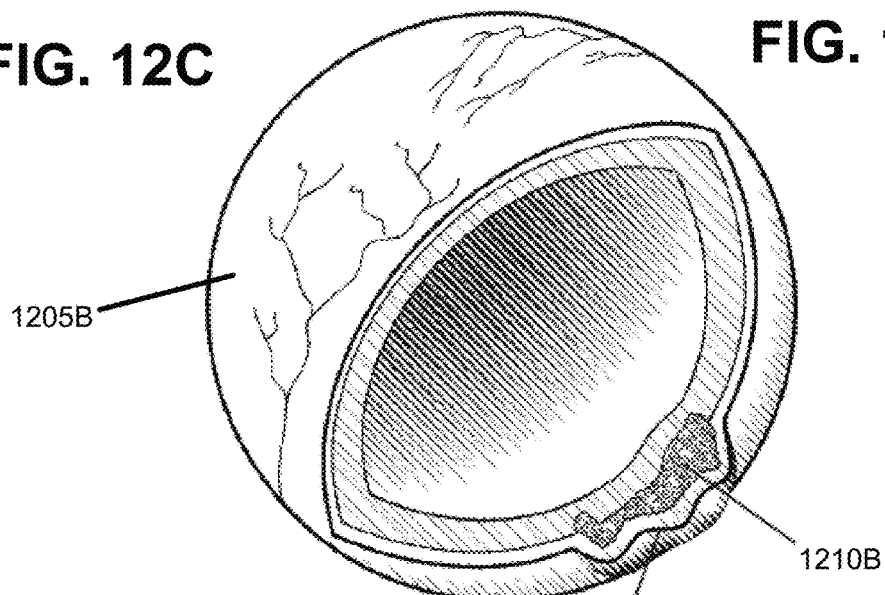
FIG. 13A illustrates a second exemplary embodiment of internal cancer of an organ, such as the eye, where an internal tumor does distort a geometry of an outer wall of the organ.
Figure 13B:
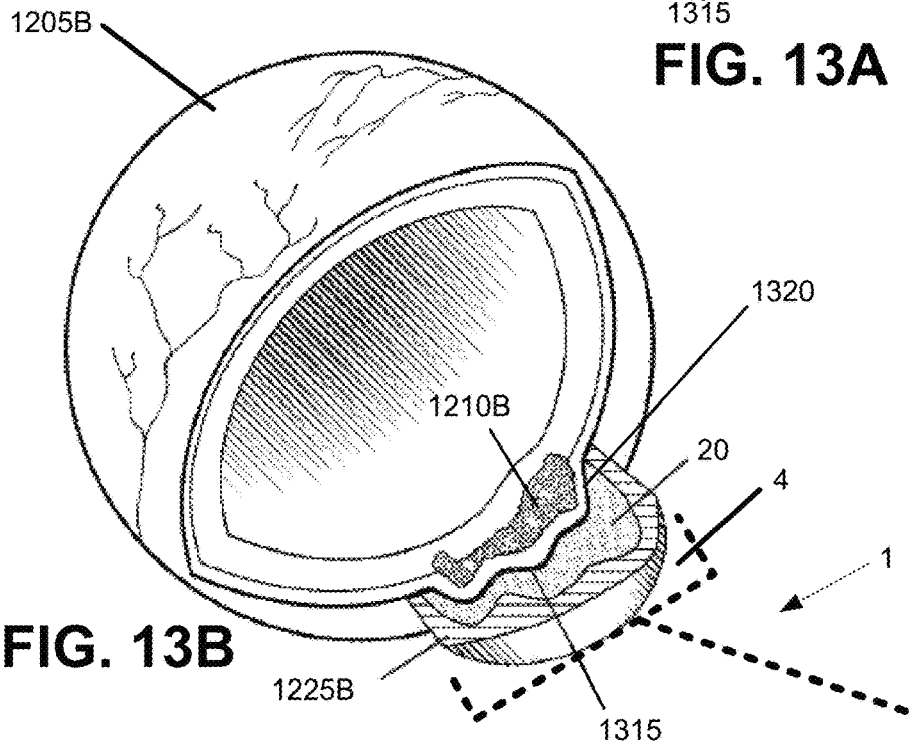
FIG. 13B illustrates a radioactive source placed adjacent to internal cancer of an organ, such as the human eye according to a second exemplary embodiment.

FIG. 12C shows a sample cross sectional view through the radiation source 1225. This FIG. 12C shows the source material 20 the substrate or container shell 1225A, and the variable thickness source material 20, is custom made to match to the patient's tumor characteristics, and specifically the unique external and internal geometry of the tumor 1210A. The source material 20 may be formed by any one of the methods described previously and illustrated in FIGS. 1-11.

Figure 12D:
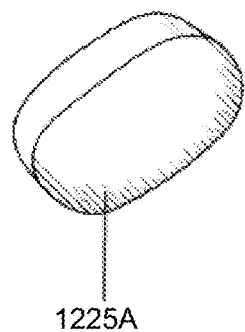
FIG. 12D illustrates an external, perspective view of the radioactive source shown in FIGS. 12A-12C.

FIG. 12D illustrates an external, perspective view of the container shell 1225A. The external view of FIG. 12D shows how the external shell 1225A may have a regular geometry having one or more lines of symmetry. Meanwhile, as illustrated in FIG. 12C described above, the internal source or source material 20 may comprise an irregular geometry which may or may not have any lines of geometrical symmetry.

Referring now to FIG. 13A, this figure illustrates a tumor 1210B which creates a protruding, convex contour or surface geometry 1315, (or in other instances not illustrated—a depressed or concave contour). As illustrated in FIG. 13B, a face or surface geometry 1320 of the radioactive source material 20 is contoured in its manufacture to conform to the irregularities present in the external geometry and internal geometry of the tumor 1210B. This data for the external geometry and internal geometry of the tumor 1210B may be derived from a variety of sources including photography, but most advantageously from three-dimensional (3D) datasets from magnetic resonance imaging (MRI), computed tomography (CT) scan data, or other medical imaging techniques capable of producing such 3D data.

In FIG. 13A, an organ 1205B having an internal tumor 1210B creating an irregular protruding geometry 1315 of the organ 1205B that would otherwise make brachytherapy difficult is illustrated. In FIG. 13B, a source 20 that has been manufactured to have its mating surface 1320 conform to the irregularities in the surface geometry 1315 of the organ 1205B so as to make close contact across the mating surface 1320 between the source 20 and the irregular surface geometry 1315. As noted above, the container 1225B may be placed in the cavity 4 of wand 3 as illustrated in FIGS. 1A and 1D.

Also illustrated in FIG. 13B is a medical device 1 shown with dashed lines which may comprise the cavity 4 described above in connection with FIG. 1D. The medical device 1 of FIG. 13B is a mere representation [oversimplification] of the ophthalmic treatment device 1 illustrated in FIG. 1D. Other medical devices 1 besides the ophthalmic treatment device 1 are possible for treating other types of cancer as described above and are included within the scope of this disclosure as understood by one of ordinary skill in the art.

Figure 13C:
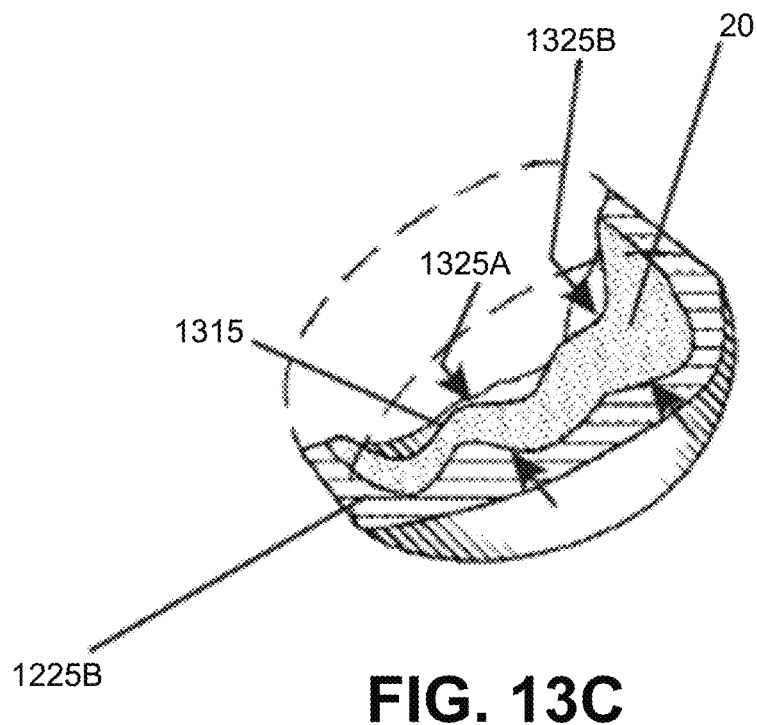
FIG. 13C illustrates a cross sectional view of the radioactive source shown in FIGS. 13A-13B.

In FIG. 13C, the source 20 has variations in its thickness at different locations 1325A, 1325B across the width dimension of the source 20. These correspond with the therapeutic requirements for the internal tumor 1210B as relates to the variable tumor geometries (both internal and external) needing radioactive irradiation treatment. In other words, both the contact/mating surface 1320 and the thickness of the source 20, as shown by locations 1325A, 1325B of FIG. 13B, are manufactured as controlled contours based on contour conformity and dose conformity corresponding to the unique geometry of the internal tumor 1210B. As noted above, the substrate or container shell 1225B is formed to hold the radiation source material 20 and provide any necessary geometrical features/contours for placement and/or anchoring to the organ 1205 so as to be in very dose proximity to the internal tumor 1210B.

Figure 13D:
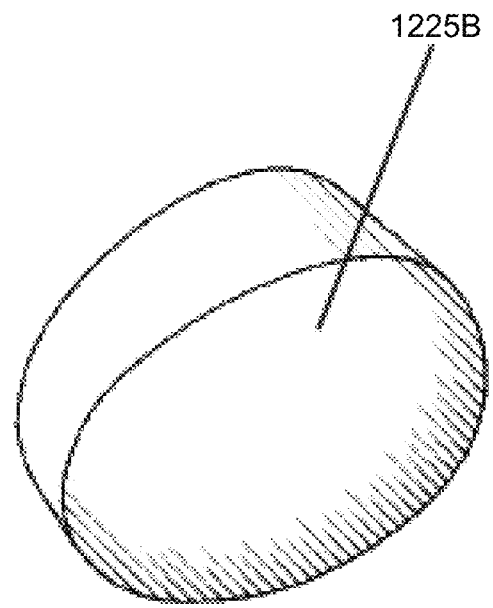
FIG. 13D illustrates an external, perspective view of the radioactive source shown in FIGS. 13A-13C.

FIG. 13D illustrates an external, perspective view of the container shell 1225B. The external view of FIG. 13D, like FIG. 12D, shows how the external shell 1225B may have a regular geometry having one or more lines of symmetry—opposite to the source material 20 contained therein. Specifically, as illustrated in FIG. 13C described above, the internal source or source material 20 may comprise an irregular geometry which may or may not have any lines of geometrical symmetry.

Figure 13E:
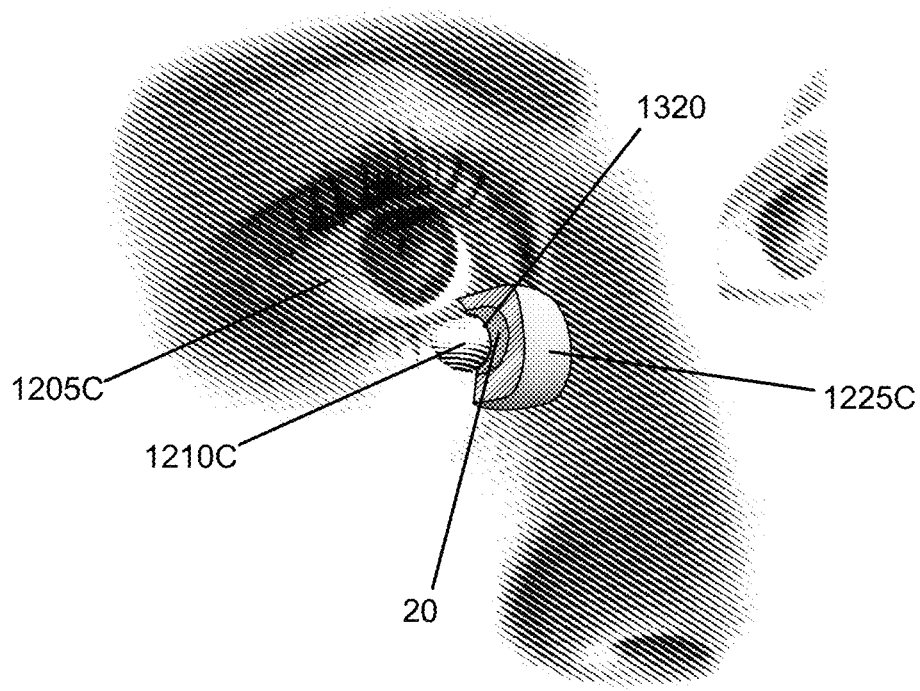
FIG. 13E illustrates a source that has been manufactured to have its mating surface conform to the irregularities in the surface geometry of an external tumor growing external relative to the organ of the eye.

Referring now to FIG. 13E, this figure illustrates a source 20 that has been manufactured to have its mating surface 1320 conform to the irregularities in the surface geometry of a tumor 1210C growing external relative to the organ 1205C of the eye. This conforming shape of the mating surface 1320 of the source 20 facilitates dose contact between the source 20 and the irregular surface geometry of the external tumor 1210C. Like FIG. 13E, the irregularly shape source 20 may have a regularly shaped container/shell 1225C that may have one or more lines of geometrical symmetry while the source 20 may not have any lines of symmetry or far less relative to the container 1225C. As noted above, the container 1225C may be placed in the cavity 4 of wand 3 as illustrated in FIGS. 1A and 1D. The container 1225C may have contoured geometries/geometrical features that mirror an organ 1205 and/or a tumor 1210 to facilitate closer coupling of the container 1225C to human tissue.

Figure 13F:
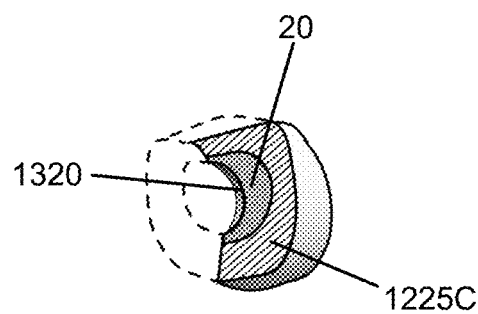
FIG. 13F illustrates the source of FIG. 13E having variations in its thickness at different locations across the width dimension of the source.

In FIG. 13F, the source 20 has variations in its thickness at different locations across the width dimension of the source 20. These correspond with the therapeutic requirements for the external tumor 1210C of FIG. 13E as relates to the variable tumor geometries (both internal and external) needing radioactive irradiation treatment. In other words, both the contact/mating surface 1320 and the thickness of the source 20 are manufactured as controlled contours based on contour conformity and dose conformity corresponding to the unique geometry of the external tumor 1210C. As noted above, the substrate or container shell 1225C is formed to hold the radiation source material 20 and may provide any necessary geometrical features/contours for placement and/or anchoring directly to the external tumor 1210C (of FIG. 13E).

Figure 13G:
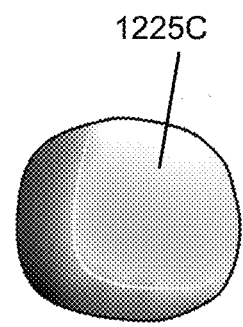
FIG. 13G illustrates an external, perspective view of the container shell of FIGS. 13E and 13F.

FIG. 13G illustrates an external, perspective view of the container shell 1225C of FIGS. 13E and 13F. The external view of FIG. 13G, like FIG. 12D, shows how the external shell 1225C for the source 20 may have a regular geometry having one or more lines of symmetry—opposite to the irregular shaped source material 20 contained therein. Specifically, as illustrated in FIG. 13G described above, the internal source or source material 20 may comprise an irregular geometry which may or may not have any lines of geometrical symmetry or far fewer relative to the several geometrical lines of symmetry present in the shell/container 1225C.

The shell container 1225C is not limited to its regular/normal geometry. Each source container 1225 may have a shape related to both its shielding requirements and the use requirements. For example, like the source material 20, the container may be designed/shaped to fit around anatomical features such as shown in 13E where it may fit around the eyelid, and clears the nose, plus other features arising from use requirements, such as mounting, grasping or suturing eyelets for example.

Figure 14:
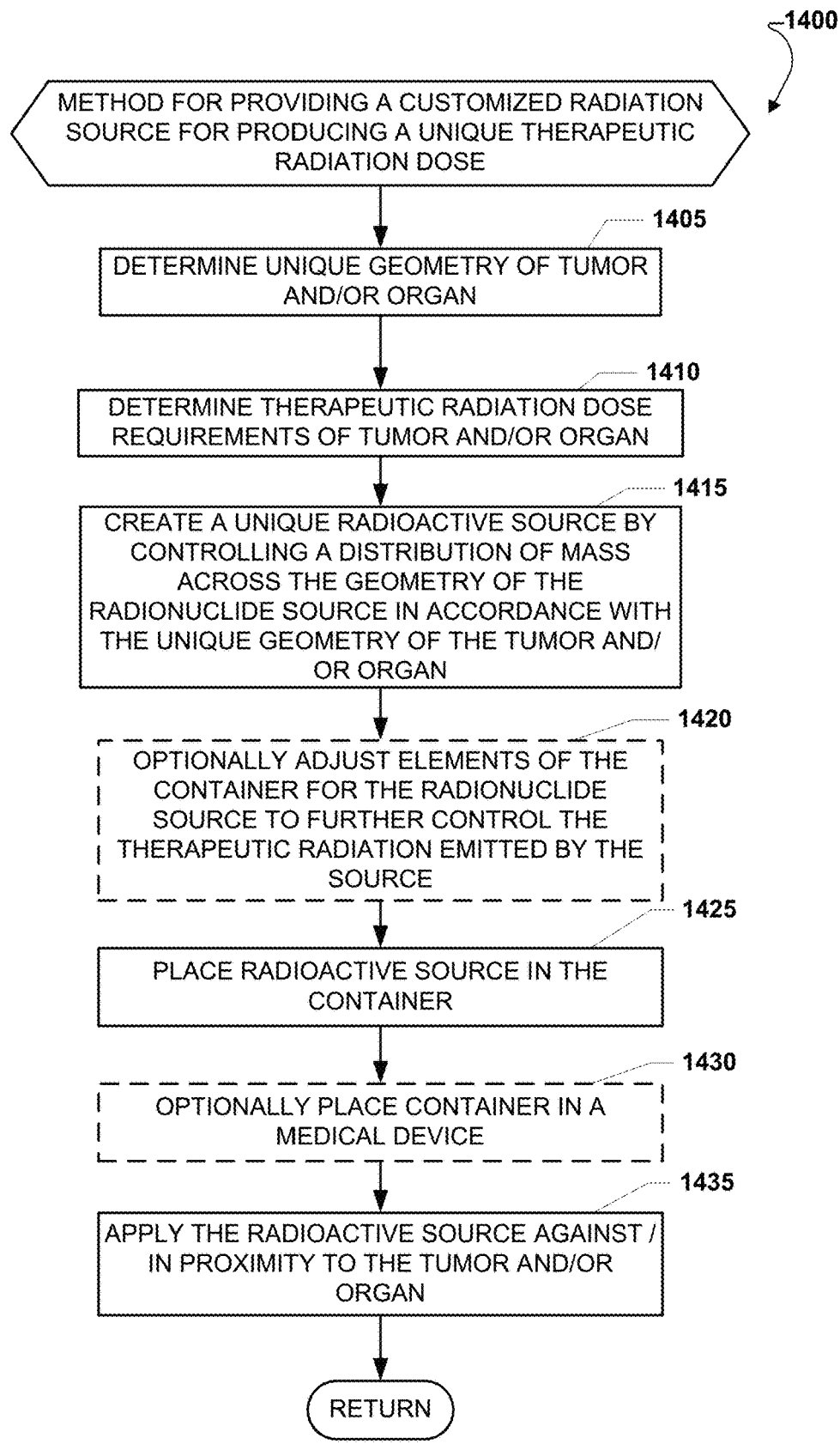
FIG. 14 illustrates an exemplary method for providing a customized radiation source for producing a unique therapeutic radiation dose corresponding to FIGS. 1-13.

Referring now to FIG. 14, this figure illustrates an exemplary method 1400 for providing a customized radiation source for producing a unique therapeutic radiation dose. Block 1405 is the first step of the exemplary method 1400 in which a unique geometry of a tumor 1210 and/or organ 1205 may be determined/calculated. According to one exemplary embodiment, data for the external geometry and internal geometry of a tumor 1210 and/or organ may be derived from a variety of sources including photography, but most advantageously from three-dimensional (3D) datasets from magnetic resonance imaging (MRI), computed tomography (CT) scan data, or other medical imaging techniques capable of producing such 3D data.

Next, in step 1410 the therapeutic radiation dose requirements for the tumor 1210 and/or organ 1205 may be determined. A general purpose computer running a specific application program and/or a medical practitioner may assess what levels of therapeutic radiation should be applied to the tumor 1210 and/or organ 1205 based on the data collected in Step 1405.

Subsequently, in step 1415, a unique radioactive source 20 may be prepared by controlling a distribution of mass across the geometry of the radionuclide source material 20 in accordance with the unique geometry found in step 14015. Generally, the unique radioactive source 20 may be prepared according to any one and/or combination of structures illustrated in FIGS. 1B-1C, 1E-1F, and 2A-6D described above.

In step 1420, elements of the container 25 for the radionuclide source 20 may be optionally adjusted in order to further control the therapeutic radiation emitted by the radioactive source 20. Generally, the container 25 may be prepared according to any one and/or combination of structures illustrated in FIGS. 7-11E described above.

Next, in step 1425, the radioactive source 20 is placed into the container 25. In optional step 1430, the container 25 is then placed in a cavity 4 of a medical device 1, such as illustrated in FIG. 1D, in step 1430. Step 1430 is optional since a medical device may not be needed to position the container 25 adjacent to or in proximity to the tumor 1210 and/or organ. Other structures besides medical devices 1 could be deployed without departing from this disclosure. For example, a bandage, an adhesive, or some other physical structure may be used to position the container 25 adjacent to or in proximity to the tumor 1210 and/or organ 1205. Further, the container 25 may be manufactured to have a structure for fastening itself adjacent or in proximity to the tumor 1210 or organ 1205.

In step 1435, the radioactive source 20 within the container 25 is then placed against and/or in proximity of the tumor 1210 and/or organ 1205. See for example the exemplary embodiments illustrated in FIGS. 12B, 13B, and 13E. The process 1400 then returns where the steps may be repeated.

The exemplary embodiments of the inventive method and system described above are interchangeable as understood by one of ordinary skill in the art. Various embodiments may be combined with other embodiments without departing from the scope of this disclosure. That is, one or more embodiments illustrated in the several figures may be combined together. As but one non-limiting example, the exemplary embodiments illustrated in FIG. 2C and FIG. 2D could be combined. Thus, a source 20 may be produced that includes a combination of holes 35C [from FIG. 2C] and slots 35D [from FIG. 2D]. Other combinations of the exemplary embodiments are possible and are included within the scope of this disclosure.

Certain steps in the exemplary methods described herein naturally precede others for the invention to function as described. However, the invention is not limited to the order of the steps described if such order or sequence does not alter the functionality of the system and methods of the present disclosure. That is, it is recognized that some steps may performed before, after, or parallel (substantially simultaneously with) other steps without departing from the scope and spirit of the invention. In some instances, certain steps may be omitted or not performed without departing from the invention. Further, words such as "thereafter", "then", "next", etc. are not intended to limit the order of the steps. These words are simply used to guide the reader through the description of the exemplary methods.

Alternative embodiments for the system and method of the present disclosure will become apparent to one of ordinary skill in the art to which the invention pertains without departing from the scope of this disclosure.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, sixth paragraph for any limitations of any of the claims herein, except for those in which the claim expressly uses the words 'means for' together with an associated function.

Therefore, although selected aspects have been illustrated and described in detail, it will be understood that various substitutions and alterations may be made therein without departing from the spirit and scope of the present invention, as defined by the following claims.

What is claimed is:

1. A system for providing a radiation source producing a radiation field, the system comprising:
    a radioactive source with a first geometry and first perimeter defining its first geometry, the radioactive source having material generally spanning an area bounded by the first perimeter, the radioactive source having a first thickness dimension and a first width dimension; and
    a container for enveloping the radioactive source, the container having a second thickness dimension and a second width dimension, the second thickness dimension being greater than the first thickness dimension, the second width dimension being greater than the first width dimension, the container being formed from a three dimensional printing process and a three dimensional printed material, the three dimensional printed material comprising a metal impregnated compound, the container further comprising a contour that makes the second thickness dimension an irregular shape and causes variable dose rate emissions across a face of the radioactive source.

2. The system of claim 1, wherein the radioactive source comprises at least one of: $^{90}$Sr, $^{169}$Yb, $^{90}$Y, $^{192}$Ir, $^{103}$Pd, $^{177}$Lu, $^{149}$Pm, $^{140}$La, $^{153}$Sm, $^{186}$Re, $^{188}$Re, $^{166}$Ho, $^{166}$Dy, $^{137}$Cs, $^{57}$Co, $^{169}$Er, $^{165}$Dy, $^{97}$Ru, $^{193m}$Pt, $^{195m}$Pt, $^{105}$Rh, $^{68}$Ni, $^{67}$C, $^{64}$Cu, $^{109}$Cd, $^{111}$Ag, $^{198}$Au, $^{199}$Au, $^{201}$Tl, $^{175}$Yb, $^{47}$Sc, $^{159}$Gd, and $^{212}$Bi.

3. The system of claim 1, wherein the first geometry comprises a disc, and wherein the container comprises a cylindrical geometry.

4. The system of claim 1, wherein the metal impregnated compound comprises: at least one of tungsten, stainless steel, or lead.

5. The system of claim 4, wherein the metal impregnated compound has a first shielding density relative to the radiation field produced by the radiation source, the container further comprising a material having a second shielding density lower relative to the first shielding density.

6. The system of claim 5, wherein the contour is a first contour, the material having the second shielding density also comprises a second contour that causes variable dose rate emissions across the face of the radioactive source.

7. The system of claim 6, wherein the material having the second shielding density contacts the radioactive source.

8. The system of claim 6, wherein the material having the second shielding density does not contact the radioactive source and only contacts the metal impregnated compound.

9. The system of claim 1, wherein the radioactive source is formed by three dimensional printing.

10. The system of claim 1, wherein the container has a geometry that matches at least one of a tumor and an organ.

11. The system of claim 1, further comprising a medical device, the medical device comprising a cavity in which the container is positioned.

12. The system of claim 1, wherein the medical device is a hand-held device.

13. The system of claim 12, wherein the hand-held device comprises a wand and a handle used in brachytherapy.

14. A system for providing a radiation source producing a radiation field, the system comprising:
a radioactive source with a first geometry and first perimeter defining its first geometry, the radioactive source having material generally spanning an area bounded by the first perimeter, the radioactive source having a first thickness dimension and a first width dimension, the radioactive source comprises a source that emits beta radiation particles; and
a container for enveloping the radioactive source, the container having a second thickness dimension and a second width dimension, the second thickness dimension being greater than the first thickness dimension, the second width dimension being greater than the first width dimension, the container being formed from a three dimensional printing process and a three dimensional printed material, the three dimensional printed material comprising a metal impregnated compound, the container further comprising a contour that makes the second thickness dimension an irregular shape and causes variable dose rate emissions across a face of the radioactive source.

15. The system of claim 14, wherein the first geometry comprises a disc, and wherein the container comprises a cylindrical geometry.

16. The system of claim 14, wherein the metal impregnated compound comprises: at least one of tungsten, stainless steel, or lead.

17. The system of claim 16, wherein the metal impregnated compound has a first shielding density relative to the radiation field produced by the radiation source, the container further comprising a material having a second shielding density lower relative to the first shielding density.

18. The system of claim 17 wherein the contour is a first contour, the material having the second shielding density also comprises a second contour that causes variable dose rate emissions across the face of the radioactive source.

19. The system of claim 18, wherein the material having the second shielding density contacts the radioactive source.

20. The system of claim 18, wherein the material having the second shielding density does not contact the radioactive source and only contacts the metal impregnated compound.

\* \* \* \* \*